United States Patent
Gerlach et al.

(10) Patent No.: US 7,230,103 B2
(45) Date of Patent: Jun. 12, 2007

(54) SUBSTITUTED 3,4-DIHYDROPYRIDO[1,2-A]PYRIMIDINES

(75) Inventors: Matthias Gerlach, Brachttal (DE); Corinna Maul, Aachen (DE); Utz-Peter Jagusch, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/411,390

(22) Filed: Apr. 11, 2003

(65) Prior Publication Data

US 2003/0229104 A1 Dec. 11, 2003

Related U.S. Application Data

(63) Continuation of application No. PCT/EP01/11700, filed on Oct. 10, 2001.

(30) Foreign Application Priority Data

Oct. 13, 2000 (DE) .............. 100 50 662

(51) Int. Cl.
*A01N 43/90* (2006.01)
*A61K 31/519* (2006.01)
(52) U.S. Cl. .............. 544/282; 514/259.4; 514/259.41; 544/283
(58) Field of Classification Search ............. 514/259.4, 514/259.41; 544/282
See application file for complete search history.

(56) References Cited

U.S. PATENT DOCUMENTS 4,291,036 A 9/1981 Knoll et al. ............. 514/259.4

FOREIGN PATENT DOCUMENTS

EP 0182569 1/1992

OTHER PUBLICATIONS

Brunello N, Mendlewicz J, Kasper S, Leonard B, Montgomery S, Nelson J, Paykel E, Versiani M, Racagni G., Eur Neuropsychopharmacol. Oct. 2002;12(5):461-75.*
Iyengar S, Webster AA, Hemrick-Luecke SK, Xu JY, Simmons RM., J Pharmacol Exp Ther. Nov. 2004;311(2):576-84.*
Montgomery SA., Int Clin Psychopharmacol. May 1999;14 Suppl 1:S21-6 MEDLINE abstract PMID: 10468325.*
Kasper S, el Giamal N, Hilger E., Expert Opin Pharmacother. May 2000;1(4):771-82 MEDLINE abstract PMID: 11249515.*
Tisler, et al., Pyrimido[1,2-b]pyrimidazines, Journal of Organic Chemistry, 36(17), 2457-62 (1971).*
Alan R. Katrizky, et al., "A Novel Facile Method for the Synthesis of 3,4-Dihydro-2H-pyridol (1,2-a) pyrimidinium Salts" Short Papers, Synthesis 1998, pp. 704-706.
F. Fuelop, et al., "Nitrogen Bridegehead Compounds" Pharmazie 38, 1983, vol. 4, pp. 218-220.
L. S. Povarov, "Reaction of pyridylimines of aromatic aldehydes with unsaturated ethers" Chemical Heterocycl. Compounds, vol. 15, 1979, p. 1369.
M. A. Abdel-Rahman, "Invers electron demand diels-alder reactions of 2-(arylmethyleneamin)-pyridines with enamines and styrenes. Synthesis of pyramidine derivatives" Revue Roumaine of Chimie, vol. 40, 1995, pp. 535-540.
Chemical Abstracts: vol. 127, 1997, Ref. 275116d.
Chemical Abstracts: vol. 126, 1997, Ref. 171887u.
Chemical Abstracts: vol. 128, 1998, Ref. 294752v.
Chemical Abstracts: vol. 92, 1980, Ref. 110889d.
Chemical Abstracts: vol. 124, 1996, Ref. 260974w.
Chemical Abstracts: vol. 124, 1996, Ref. 250537s.

* cited by examiner

*Primary Examiner*—Zachary C. Tucker
*Assistant Examiner*—Erich A. Leeser
(74) *Attorney, Agent, or Firm*—Crowell & Moring LLP

(57) ABSTRACT

Substituted 3,4-dihydropyrido[1,2-a]pyrimidines of formula I

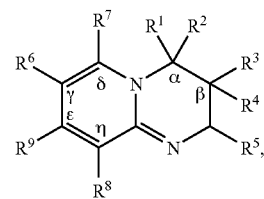

and processes for the production thereof Also disclosed are substance libraries and pharmaceutical compositions containing the compound, and methods of treatment for pain, urinary incontinence, pruritus, tinnitus and/or diarrhoea using the pharmaceutical composition.

14 Claims, No Drawings

SUBSTITUTED 3,4-DIHYDROPYRIDO[1,2-A]PYRIMIDINES

CROSS REFERENCE TO RELATED APPLICATIONS

The present application is a continuation of International Patent Application No. PCT/EP01/11700, filed Oct. 10, 2001, designating the United States of America and published in German as WO 02/30933 A1, the entire disclosure of which is incorporated herein by reference. Priority is claimed based on Federal Republic of Germany Patent Application No. 100 50 662.3, filed Oct. 13, 2000.

FIELD OF THE INVENTION

The present application relates to substituted 3,4-dihydropyrido[1,2-a]pyrimidines, to processes for the production thereof, to substance libraries containing them, to pharmaceutical preparations containing these compounds, to the use of these compounds for the production of pharmaceutical preparations, and methods for the treatment of pain, urinary incontinence, pruritus, tinnitus and/or diarrhea and to pharmaceutical compositions containing these compounds.

BACKGROUND OF THE INVENTION

The treatment of chronic and non-chronic pain is of great significance in medicine. There is a worldwide requirement for effective therapeutic methods for providing tailored and targeted treatment of chronic and non-chronic pain, especially effective and satisfactory pain treatment from the patient's standpoint.

Conventional opioids such as morphine are highly effective in treating severe to very severe pain. However, their use is limited by known side-effects such as respiratory depression, vomiting, sedation, constipation and development of tolerance. Moreover, they are less effective in treating neuropathic or incidental pain, which is in particular experienced by tumor patients.

DESCRIPTION OF THE INVENTION

An object of the present invention is to provide analgesically active compounds suitable for pain therapy, in particular for treating chronic and neuropathic pain. Furthermore, these substances should as much as possible not cause any of the side-effects which occur when using opioids with P-receptor affinity (e.g. morphine), such as nausea, vomiting, dependency, respiratory depression or constipation.

This object is achieved by the compounds of the general formula I which are analgesically active. The compounds according to the invention comprise substituted 3,4-dihydropyrido[1,2-a]pyrimidines of the general formula I

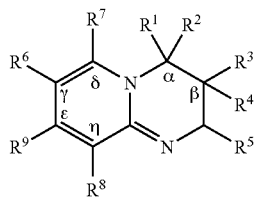

in which
$R^1$ and $R^2$ mutually independently mean H; $OR^{10}$; SH; $SR^{10}$; $C_{1-12}$ alkyl, which is linear or branched and is saturated or unsaturated and is unsubstituted or mono- or polysubstituted; $C_{3-8}$ cycloalkyl, which is saturated or unsaturated and is unsubstituted or mono- or polysubstituted; aryl, which is unsubstituted or mono- or polysubstituted; heteroaryl, which is unsubstituted or mono- or polysubstituted, ($C_{1-6}$ alkyl)aryl, wherein the $C_{1-6}$ alkyl is linear or branched and is saturated or unsaturated and is unsubstituted or mono- or polysubstituted, and the aryl is unsubstituted or mono- or polysubstituted; or ($C_{1-6}$ alkyl)heteroaryl, wherein the $C_{1-6}$ alkyl is linear or branched and is saturated or unsaturated and is unsubstituted or mono- or polysubstituted, and the heteroaryl is unsubstituted or mono- or polysubstituted, wherein one of $R^1$ and $R^2$ is H and the other of $R^1$ and $R^2$ is not H, provided that, if one of $R^1$ and $R^2$ means aryl, the other of $R^1$ and $R^2$ means H or $C_{1-12}$ alkyl, $R^3$ and $R^4$ mutually independently mean H; $C_{1-12}$ alkyl, which is linear or branched and is saturated or unsaturated and is unsubstituted or mono- or polysubstituted; $C_{3-8}$ cycloalkyl, which is saturated or unsaturated and is unsubstituted or mono- or polysubstituted; aryl, which is unsubstituted or mono- or polysubstituted; heteroaryl, which is unsubstituted or mono- or polysubstituted; ($C_{1-6}$ alkyl)aryl, wherein the $C_{1-6}$ alkyl is linear or branched and is saturated or unsaturated and is unsubstituted or mono- or polysubstituted, and the aryl is unsubstituted or mono- or polysubstituted; or ($C_{1-6}$ alkyl)heteroaryl, wherein the $C_{1-6}$ alkyl is linear or branched and is saturated or unsaturated and is unsubstituted or mono- or polysubstituted, and the heteroaryl is unsubstituted or mono- or polysubstituted, wherein at least one of $R^3$ and $R^4$ is H, or one of $R^1$ or $R^2$, together with one of $R^3$ or $R^4$, forms W, wherein W means $\alpha'$-$(CH_2)_n$-$\beta'$ where n=3, 4, 5, 6, 7, 8, 9 or 10; $\alpha'$-CH=CH—$CH_2$-$\beta'$; $\alpha'$-CH=CH—$CH_2$—$CH_2$-$\beta'$; $\alpha'$-$CH_2$—CH=CH—$CH_2$-$\beta'$; $\alpha'$-$CH_2$—$CH_2$—CH=CH—$CH_2$—$CH_2$-$\beta'$; $\alpha'$-O—$(CH_2)_n$-$\beta'$ where n=2, 3, 4, 5 or 6,

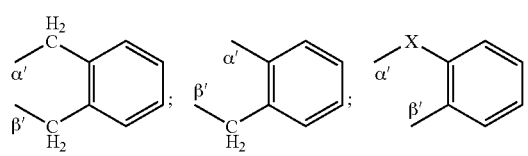

where X=$CH_2$, O or S;

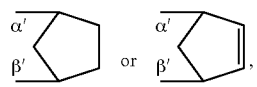

and the end of W marked $\alpha'$ is attached to the $\alpha$ carbon atom of the compound of the general formula I and the end of W marked $\beta'$ is attached to the $\beta$ carbon atom of the compound of the general formula I, the other of $R^1$ and $R^2$ is H or $C_{1-12}$ alkyl, wherein the alkyl is linear or branched and is saturated or unsaturated and is unsubstituted or mono- or polysubstituted, and the other of $R^3$ and $R^4$ is H or $C_{1-12}$ alkyl, wherein the alkyl is linear or branched and is saturated or unsaturated and is unsubstituted or mono- or polysubstituted, $R^5$ means $C_{1-12}$ alkyl, which is linear or branched and is saturated or unsaturated and is unsubstituted or mono- or polysubstituted; $C_{3-8}$ cycloalkyl, which is saturated or unsaturated and is unsubstituted or mono- or polysubstituted, aryl, wherein aryl is unsubstituted or mono- or polysubstituted; heteroaryl, which is unsubstituted or mono- or polysubstituted; $(C_{1-6}$ alkyl)aryl, wherein the $C_{1-6}$ alkyl is linear or branched and is saturated or unsaturated and is unsubstituted or mono- or polysubstituted; and the aryl is unsubstituted or mono- or polysubstituted; $(C_{1-6}$ alkyl)heteroaryl, wherein the $C_{1-6}$ alkyl is linear or branched and is saturated or unsaturated and is unsubstituted or mono- or polysubstituted, and the heteroaryl is unsubstituted or mono- or polysubstituted, $C(=O)R^{11}$, $CO_2H$ or $CO_2R^{12}$, $R^6$, $R^7$, $R8$ and $R^9$ mutually independently mean H, F, Cl, Br, I, CN, $NH_2$, $NH(C_{1-6}$ alkyl), $N(C_{1-6}$ alkyl)$_2$, $NH((C_{1-6}$ alkyl)aryl), $N((C_{1-6}$ alkyl)aryl)$_2$, $NHR^{13}$, $NO_2$, OH, SH, $O-C_{1-8}$ alkyl or $S(O)_p-C_{1-8}$ alkyl, wherein the alkyl is linear or branched and is saturated or unsaturated and is unsubstituted or mono- or polysubstituted, and p is 0, 1 or 2; O-aryl or $S(O)_q$-aryl, wherein the aryl is unsubstituted or mono- or polysubstituted and q is 0, 1 or 2; $O-(C_{1-6}$ alkyl)aryl or $S(O)_r-(C_{1-6}$ alkyl)aryl, wherein the $C_{1-6}$ alkyl is linear or branched and is saturated or unsaturated and is unsubstituted or mono- or polysubstituted, and the aryl is unsubstituted or mono- or polysubstituted and r is 0, 1 or 2; $CO_2H$, $C(=O)R^{14}$, $C_{1-12}$ alkyl, wherein the alkyl is linear or branched and is saturated or unsaturated and is unsubstituted or mono- or polysubstituted; $CF_3$, $C_{3-8}$ cycloalkyl, wherein the cycloalkyl is saturated or unsaturated and is unsubstituted or mono- or polysubstituted; heterocyclyl, which is 3-, 4-, 5-, 6- or 7-membered and is saturated or unsaturated and is unsubstituted or mono- or polysubstituted; aryl, which is unsubstituted or mono- or polysubstituted; or heteroaryl, which is unsubstituted or mono- or polysubstituted, or $R^6$ and $R^7$ together form Q, wherein Q means $\gamma'-CR^{15}=CR^{16}-CR^{17}=CR^{18}-\delta'$, the end of Q marked $\gamma'$ is attached to the $\gamma$ carbon atom of the compound of the general formula I, and the end of Q marked $\delta'$ is attached to the $\delta$ carbon atom of the compound of the general formula I, and $R^8$ and $R^9$ are defined as above, or $R^6$ and $R^9$ together form T, wherein T means $\delta'-CR^{19}=CR^{20}-CR^{21}=CR^{22}-\epsilon'$ or $\gamma'-N=CR^{20}-CR^{21}=N-\epsilon'$, the end of T marked $\gamma'$ is attached to the $\gamma$ carbon atom of the compound of the general formula I and the end of T marked $\epsilon'$ is attached to the $\epsilon$ carbon atom of the compound of the general formula I, and $R^7$ and $R^8$ are defined as above, or $R^8$ and $R^9$ together form U, wherein U means $\eta'-CR^{19}=CR^{20}-CR^{21}=CR^{22}-\epsilon'$, the end of U marked $\eta'$ is attached to the $\eta$ carbon atom of the compound of the general formula I and the end of U marked $\epsilon'$ is attached to the $\epsilon$ carbon atom of the compound of the general formula I, and $R^6$ and $R^7$ are defined as above, $R^{10}$ means $C_{1-8}$ alkyl, which is linear or branched and is saturated or unsaturated and is unsubstituted or mono- or polysubstituted; $C_{3-8}$ cycloalkyl, wherein cycloalkyl is saturated or unsaturated and is unsubstituted or mono- or polysubstituted, aryl, which is unsubstituted or mono- or polysubstituted, heteroaryl, which is unsubstituted or mono- or polysubstituted; $(C_{1-6}$ alkyl)aryl, wherein the $C_{1-6}$ alkyl is linear or branched and is saturated or unsaturated and is unsubstituted or mono- or polysubstituted; and the aryl is unsubstituted or mono- or polysubstituted; or $(C_{1-6}$ alkyl)heteroaryl, wherein the $C_{1-6}$ alkyl is linear or branched and is saturated or unsaturated and is unsubstituted or mono- or polysubstituted, and the heteroaryl is unsubstituted or mono- or polysubstituted, $R^{11}$ means $NH_2$, $NH(C_{1-6}$ alkyl), $N(C_{1-6}$ alkyl)$_2$, $NH((C_{1-6}$ alkyl)aryl), $N((C_{1-6}$ alkyl)aryl)$_2$, $C_{1-8}$ alkyl, wherein the alkyl is linear or branched and is saturated or unsaturated and is unsubstituted; or mono- or polysubstituted, $C_{3-8}$ cycloalkyl, which is saturated or unsaturated and is unsubstituted or mono- or polysubstituted; aryl, which is unsubstituted or mono- or polysubstituted; heteroaryl, which is unsubstituted or mono- or polysubstituted, $(C_{1-6}$ alkyl)aryl, wherein the $C_{1-6}$ alkyl is linear or branched and is saturated or unsaturated and is unsubstituted or mono- or polysubstituted, and the aryl is unsubstituted or mono- or polysubstituted; or $(C_{1-6}$ alkyl)heteroaryl, wherein the $C_{1-6}$ alkyl is linear or branched and is saturated or unsaturated and is unsubstituted or mono- or polysubstituted, and the heteroaryl is unsubstituted or mono- or polysubstituted, $R^{12}$ means $C_{1-8}$ alkyl, which is linear or branched and is saturated or unsaturated and is unsubstituted or mono- or polysubstituted; $C_{3-8}$ cycloalkyl, which is saturated or unsaturated and is unsubstituted or mono- or polysubstituted; $(C_{1-6}$ alkyl)aryl, wherein the $C_{1-6}$ alkyl is linear or branched and is saturated or unsaturated and is unsubstituted or mono- or polysubstituted, and the aryl is unsubstituted or mono- or polysubstituted, $R^{13}$ means $C(=O)CH_3$, $C(=O)$phenyl, $C(=O)O$-t.-butyl (t-BOC) or another conventional amino protective group, $R^{14}$ means H, $NH_2$, $NH(C_{1-6}$ alkyl), $N(C_{1-6}$ alkyl)$_2$, $NH((C_{1-6}$ alkyl)aryl), $N((C_{1-6}$ alkyl)aryl)$_2$, $C_{1-8}$ alkyl, wherein the alkyl is linear or branched and is saturated or unsaturated and is unsubstituted or mono- or polysubstituted; $C_{3-8}$ cycloalkyl, which is saturated or unsaturated and is unsubstituted or mono- or polysubstituted; aryl, which is unsubstituted or mono- or polysubstituted; or $(C_{1-6}$ alkyl)aryl, wherein the $C_{1-6}$ alkyl is linear or branched and is saturated or unsaturated and is unsubstituted or mono- or polysubstituted, and the aryl is unsubstituted or mono- or polysubstituted; $OC_{1-8}$ alkyl, wherein the alkyl is linear or branched and is saturated or unsaturated and is unsubstituted or mono- or polysubstituted; $OC_{3-8}$ cycloalkyl, wherein the cycloalkyl is saturated or unsaturated and is unsubstituted or mono- or polysubstituted; O-aryl, wherein the aryl is unsubstituted or mono- or polysubstituted; or $O-(C_{1-6}$ alkyl)aryl, wherein the $C_{1-6}$ alkyl is linear or branched and is saturated or unsaturated and is unsubstituted or mono- or polysubstituted, and the aryl is unsubstituted or mono- or polysubstituted, $R^{15}$, $R^{16}$, $R^{17}$ and $R^{18}$ mutually independently mean H, F, Cl, Br, I, CN, OH, $C_{1-8}$ alkyl, wherein the alkyl is linear or branched and is saturated or unsaturated and is unsubstituted or mono- or polysubstituted, or $CO_2H$, and $R^{19}$, $R^{20}$, $R^{21}$ and $R^{22}$ mutually independently mean H, F, Cl, Br, I, CN, OH, $C_{1-8}$ alkyl, wherein the alkyl is linear or branched and is saturated or unsaturated and is unsubstituted or mono- or polysubstituted, or $CO_2H$, or the pharmaceutically acceptable salts thereof.

The following compounds of the general formula I are already known in the prior art, without the use thereof having been described in a pharmaceutical preparation or for the production of a pharmaceutical preparation for the treatment of pain, urinary incontinence, pruritus, tinnitus and/or diarrhea. These known compounds include 6-chloro-2-(4-nitrophenyl)-4-phenyl-3,4-dihydro-2H-pyrido[1,2-a]pyrimidine, 2-(4-nitrophenyl)-4-phenyl-3,4-dihydro-2H-pyrido[1,2-a]pyrimidine, 2-(2-nitrophenyl)-4-phenyl-3,4-dihydro-2H-pyrido[1,2-a]pyrimidine, 2-(4-nitrophenyl)-4-(4-tolyl)-3,4-dihydro-2H-pyrido[1,2-a]pyrimidine and 2-(4-chlorophenyl)-(4-(4-tolyl)-3,4-dihydro-2H-pyrido[1,2-a] pyrimidine, which have been described by M. A. Abdel-Rahman, *Revue Roumaine de Chimie* 40, 535–540 (1995); 4-ethoxy-2-phenyl-3,4-dihydro-2H-pyrido[1,2-a]pyrimidine and 4-ethoxy-2-(2-hydroxyphenyl)-3,4-dihydro-2H-pyrido[1,2-a]pyrimidine, which have been described by L. S. Povarov, *Chem. Heterocycl. Comp.* 15, 1369 (1979) (C. A. 92 (1980), 110889); 4-ethoxy-2-propyl-3,4-dihydro-2H-pyrido[1,2-a]pyrimdinem, 4-propyl-2,3,3a,4,5,10a-hexahydro-2H-pyrido[1,2-a]furo[3,2-e]pyrimidine and 4-propyl-2,4,4a,5,6,11a-hexahydro-2H-pyrido[1,2-a]pyrano[3,2-e] pyrimidine, which have been described by A. R. Katritzky, G Qin, B. Yang, *Synthesis* 1998, 704–706.

For the purposes of the present invention, the terms "$C_{1-6}$ alkyl", "$C_{1-8}$ alkyl" and "$C_{1-12}$ alkyl" comprise acyclic saturated or unsaturated hydrocarbon residues, which may be branched or linear and unsubstituted or mono- or polysubstituted, respectively comprising 1 to 6, 1 to 8 and 1 to 12 carbon atoms, i.e. $C_{1-6}$ alkanyls, $C_{2-6}$ alkenyls and $C_{2-6}$ alkynyls, $C_{1-8}$ alkanyls, $C_{2-8}$ alkenyls and $C_{2-8}$ alkynyls and $C_{1-12}$ alkanyls, $C_{2-12}$ alkenyls and $C_{2-12}$ alkynyls. Alkenyls here comprise at least one C—C double bond and alkynyls at least one C—C triple bond. Alkyl is advantageously selected from the group comprising methyl, ethyl, n-propyl, 2-propyl, n-butyl, isobutyl, sec.-butyl, tert.-butyl, n-pentyl, iso-pentyl, neopentyl, n-hexyl, 2-hexyl, n-octyl, n-decyl, n-dodecyl; ethylenyl (vinyl), ethynyl, propenyl (—$CH_2CH$=$CH_2$, —CH=CH—$CH_3$, —C(=$CH_2$)—$CH_3$propynyl,(—CH—C≡CH), butenyl, butynyl, pentenyl, hexenyl, hexynyl, octenyl and octynyl.

For the purposes of the present invention, the term "$C_{3-8}$ cycloalkyl" means cyclic hydrocarbons with 3 to 8 carbon atoms, which may be saturated or unsaturated, unsubstituted or mono- or polysubstituted. $C_{3-8}$ cycloalkyl is advantageously selected from the group which contains cyclopropyl, cyclobutyl, cyclopentyl, cyclohexyl, cycloheptyl, cyclooctyl, cyclopentenyl, cyclohexenyl, cycloheptenyl and cyclooctenyl. Cyclopropyl, cyclopropyl-2-carboxylic acid, cyclopropyl-2-carboxylic acid ethyl ester and cyclohexyl are particularly preferred for thr purposes of the present invention.

For the purposes of the present invention, the term "aryl" means aromatic hydrocarbons, inter alia phenyls, naphthyls and anthracenyls. The aryl residue may also be fused with further saturated, (partially) unsaturated or aromatic ring systems. Each aryl residue may be present in unsubstituted or mono-or polysubstituted form, wherein the aryl substituets may be identical or different and be in any desired position of the aryl. Aryl is advantageously selected from the group which contains phenyl, 1-naphthyl and 2-naphthyl. For thr purposes of the invention, particularly preferred aryl residues are m-toluyl, p-hydroxyphenyl, p-methoxyphenyl, 4-hydroxy-3-methoxyphenyl, 2,4-dimethylphenyl, 4-fluorophenyl, 1-naphthyl and 2-naphthyl.

The term "heteroaryl" denotes a 5-, 6- or 7-membered cyclic aromatic residue, which contains at least 1, optionally also 2, 3, 4 or 5 heteroatoms, wherein the heteroatoms are identical or different and the heterocycle may be unsubstituted or mono- or polysubstituted; in the event of substitution on the heterocycle, the heteroaryl substituents may be identical or different and be in any possible position of the heteroaryl. The heterocycle may also be part of a bi- or polycyclic system. Preferred heteroatoms are nitrogen, oxygen and sulfur. It is preferred for the heteroaryl to be selected from among the group comprising pyrrolyl, indolyl, furyl (furanyl), benzofuranyl, thienyl (thiophenyl), benzothienyl, pyrazolyl, imidazolyl, thiazolyl, oxazolyl, isoxazoyl, pyridinyl, pyridazinyl, pyrimidinyl, pyrazinyl, pyranyl, indolyl, indazolyl, purinyl, pyrimidinyl, indolizinyl, quinolinyl, isoquinolyl, quinazolinyl, carbazolyl, phenazinyl, phenothiazinyl, wherein the bond to the compounds of the general formula I (or II, III or IV) may be made via any desired and possible ring member of the heteroaryl residue. For the purposes of the present invention, particularly preferred heteroaryl residues are 2-pyridinyl, 2-furanyl, 5-methyl-2-furanyl and 5-nitro-2-furanyl.

For the purposes of the present invention, the terms "($C_{1-6}$ alkyl)aryl" and "($C_{1-6}$ alkyl)heteroaryl" mean that $C_{1-6}$ alkyl, aryl and heteroaryl have the above-defined meanings and are attached via a $C_{1-6}$ alkyl group to the compound of the general formula I (or II, III or IV).

The term "heterocyclyl" denotes a 3-, 4-, 5-, 6- or 7-membered cyclic organic residue, which contains at least 1, optionally also 2, 3, 4 or 5 heteroatoms, wherein the heteroatoms are identical or different and the cyclic residue is saturated or unsaturated, but not aromatic, and may be unsubstituted or mono- or polysubstituted. The heterocycle may also be part of a bi- or polycyclic system. Preferred heteroatoms are nitrogen, oxygen and sulfur. It is preferred that the heterocyclyl residue is selected from among the group which contains tetrahydrofuryl, pyrrolidinyl, piperidinyl, piperazinyl and morpholinyl, wherein the bond to the compound of the general formula I (or II, III or IV) may be made via any desired ring member of the heterocyclyl residue.

In connection with "alkyl", "alkanyl", "alkenyl" and "alkynyl", the term "substituted" is taken for the purposes of the present invention to mean the substitution of a hydrogen residue by F, Cl, Br, I, CN, $NH_2$, NH-alkyl, NH-aryl, heteroaryl, NH-alkylaryl, NH-alkylheteroaryl, NH-heterocyclyl, NH-alkyl-OH, N(alkyl)$_2$, N(alkylaryl)$_2$, N(alkylheteroaryl)$_2$, N(heterocyclyl)$_2$, N(alkyl-OH)$_2$, NO, $NO_2$, SH, S-alkyl, S-aryl, S-heteroaryl, S-alkylaryl, S-alkylheteroaryl, S-heterocyclyl, S-alkyl-OH, S-alkyl-SH, OH, O-alkyl, O-aryl, O-heteroaryl, O-alkylaryl, O-alkylheteroaryl, O-heterocyclyl, O-alkyl-OH, CHO, C(=O)$C_{1-6}$ alkyl, C(=S)$C_{1-6}$ alkyl, C(=O) aryl, C(=S) aryl, C(=O)$C_{1-6}$ alkylaryl, C(=S)$C_{1-6}$ alkylaryl, C(=O) heteroaryl, C(=S) heteroaryl, C(=O) heterocyclyl, C(=S) heterocyclyl, $CO_2H$, $CO_2$ alkyl, C(=O)$NH_2$, C(=O)NH alkyl, C(=O)NH aryl, C(=O)NH heterocyclyl, C(=O)N(alkyl)$_2$, C(=O)N(alkylaryl)$_2$, C(=O)N(alkylheteroaryl)$_2$, C(=O)N(heterocyclyl)$_2$, SO alkyl, $SO_2$ alkyl, $SO_2NH_2$, $SO_3H$, cycloalkyl, aryl, heteroaryl or heterocyclyl. Polysubstituted residues should be taken to mean such residues which are substituted more than once either on the same or on different atoms, for example are di- or trisubstituted, for example three times on the same C atom, as in the case of $CF_3$ or —$CH_2CF_3$ or at different sites, as in the case of —CH(OH)—CH=CH—$CHCl_2$. Polysubstitution may proceed with identical or different substituents. For the purposes of the invention, methyl, ethyl, n-propyl, —$CH_2$—$CH_2$—OH or $CF_3$ are particularly preferred.

With regard to "aryl", "alkylaryl", "heteroaryl", "alkylheteroaryl", "heterocyclyl", and "cycloalkyl", "mono- or polysubstituted" is taken for the purposes of the present invention to mean mono- or polysubstitution, e.g. di-, tri- or tetrasubstitution of one or more hydrogen atoms of the ring system by F, Cl, Br, I, CN, $NH_2$, NH-alkyl, NH-aryl, NH-heteroaryl, NH-alkylaryl, NH-alkylheteroaryl, NH-heterocyclyl, NH-alkyl-OH, N(alkyl)$_2$, N(alkylaryl)$_2$, N(alkylheteroaryl)$_2$, N(heterocyclyl)$_2$, N(alkyl-OH)$_2$, NO, $NO_2$, SH, S-alkyl, S-cycloalkyl, S-aryl, S-heteroaryl, S-alkylaryl, S-alkylheteroaryl, S-heterocyclyl, S-alkyl-OH, S-alkyl-SH, OH, O-alkyl, O-cycloalkyl, O-aryl, O-heteroaryl, O-alkylaryl, O-alkylheteroaryl, O-heterocyclyl, O-alkyl-OH, CHO, C(=O)$C_{1-6}$ alkyl, C(=S)$C_{1-6}$ alkyl, C(=O) aryl, C(=S)

aryl, C(=O)—C$_{1-6}$ alkylaryl, C(=S)C$_{1-6}$ alkylaryl, C(=O) heteroaryl, C(=S) heteroaryl, C(=O) heterocyclyl, C(=S) heterocyclyl, CO$_2$H, CO$_2$ alkyl, C(=O)NH$_2$, C(=O)NH-alkyl, C(=O)NH aryl, C(=O)NH heterocyclyl, C(=O)N(alkyl)$_2$, C(=O)N(alkylaryl)$_2$, C(=O)N(alkylheteroaryl)$_2$, C(=O)N(heterocyclyl)$_2$, S(O) alkyl, S(O) aryl, SO$_2$ alkyl, SO$_2$ aryl, SO$_2$NH$_2$, SO$_3$H, cycloalkyl, aryl, heteroaryl, CF$_3$, =O, =S; C$_{1-6}$-alkanyl, C$_{2-6}$ alkenyl, C$_{2-6}$ alkynyl, —C$_{1-6}$ alkyl-C(O)O—C$_{1-6}$ alkyl; phenyl, benzyl, naphthyl and/or heterocyclyl; on one or optionally different atoms (wherein a substituent may optionally in turn itself be substituted). Polysubstitution may be with identical or different substituents. Particularly preferred substituents for aryl are F, OH, CH$_3$ and OCH$_3$. Particularly preferred substituents for heteroaryl are CH$_3$ and NO$_2$. Particularly preferred substituents for cycloalkyl are CO$_2$H and CO$_2$-ethyl.

For the purposes of the present invention, pharmaceutically acceptable salts are those salts of the compounds according to the invention of the general formula I which are physiologically compatible for pharmaceutical use, in particular for use in mammals, especially humans. Such pharmaceutically acceptable salts may, for example, be formed with inorganic or organic acids.

The pharmaceutically acceptable salts of the compounds according to the invention of the general formula I are preferably formed with hydrochloric acid, hydrobromic acid, sulfuiric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The salts formed comprise, inter alia, hydrochlorides, hydrobomides, phosphates, carbonates, hydrogencarbonates, formates, acetates, oxalates, succinates, tartrates, fumarates, citrates and glutamates. The hydrates of the compounds according to the invention, which may be obtained, for example, by crystallization from an aqueous solution, are also preferred.

All the compounds according to the invention contain at least one center of asymmetry, namely the R$^5$-substituted carbon atom of the structure I. The compound according to the invention of the general formula I may accordingly assume the form of a racemate, of a pure enantiomer or a diastereomer, or of a mixture of the enantiomer, or diastereomer as a free substance, or as the pharmaceutically acceptable salts of these compounds. The mixtures may be present in any desired mixture ratio of the stereoisomers. The compounds of the general formula I are preferably present as enantiomerically pure compounds.

Preferred compounds of the present invention are 3,4-dihydropyrido[1,2-a]pyrimidines of the general formula I, in which one of the residues R$^1$ and R$^2$ means OR$^{10}$, SR$^{10}$, C$_{1-6}$ alkyl or aryl, one of the residues R$^3$ and R$^4$ means H or C$_{1-6}$ alkyl, or one of R$^1$ and R$^2$ together with one of R$^3$ and R$^4$ form W, wherein W means

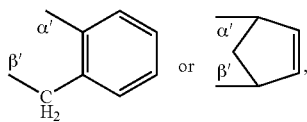

and the other two residues of R$^1$, R$^2$, R$^3$ and R$^4$ mean H or C$_{1-6}$ alkyl, R$^5$ means C$_{3-6}$ cycloalkyl, heteroaryl, C(=O)R$^{11}$, CO$_2$H or CO$_2$R$^{12}$, R$^6$ means H, F, Cl, Br, CN, NO$_2$, C(=O)R$^{14}$, C$_{1-6}$ alky, CF$_3$ or aryl, R$^7$ means H, F, Cl, Br, CN, NH$_2$, OH or C$_{1-6}$ alkyl, or R$^6$ and R$^7$ together form Q, wherein Q means γ'-CR$^{15}$=CR$^{16}$—CR$^{17}$=CR$^{18}$-δ', R$^8$ means H, F, Cl, Br, CN, NO$_2$, O—(C$_{1-6}$ alkyl)aryl, CO$_2$H, CONH$_2$ or C$_{1-6}$ alkyl, R$^9$ means H, OH, CF$_3$ or C$_{1-6}$ alkyl, or R$^8$ and R$^9$ together form U, wherein U means ε'-CH=CH—CH=CH-η', R$^{10}$ means C$_{1-8}$ alkyl or aryl, R$^{11}$ means aryl, R$^{12}$ means C$_{1-6}$ alkyl, R$^{14}$ means OC$_{1-6}$ alkyl, one or R$^{15}$, R$^{16}$, R$^{17}$ and R$^{18}$ means H or OH and the other residues of R$^{15}$, R$^{16}$, R$^{17}$ and R$^{18}$ mean H, and the pharmaceutically acceptable salts thereof.

Particularly preferred compounds of the general formula I are those in which one of the residues R$^1$ and R$^2$ means O—(CH$_2$)$_2$—OH, S-phenyl, CH$_3$, phenyl, 3-methylphenyl, 2,4-dimethylphenyl, 4-fluorophenyl, 4-hydroxyphenyl, 4-methoxyphenyl, 4-hydroxy-3-methoxyphenyl or 2-naphthyl, one of the residues R$^3$ and R$^4$ means H or methyl, or one of R$^1$ and R$^2$ together with one of R$^3$ and R$^4$ form W, wherein W means

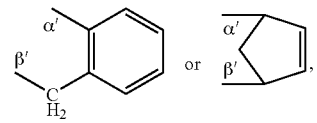

and the other two residues of R$^1$, R$^2$, R$^3$ and R$^4$ mean H, R$^5$ means cyclopropyl, 2-(C(=O)O-ethyl)-cyclopropyl, cyclohexyl, 2-pyridinyl, 5-methyl-2-furanyl, 5-nitro-2-furanyl, C(=O)phenyl, CO$_2$H or CO$_2$ethyl, R$^6$ means H, Cl, Br, CN, NO$_2$, CO$_2$ethyl, methyl, CF$_3$ or phenyl, R$^7$ means H, Cl, CN, NH$_2$, OH, methyl or n-propyl, or R$^6$ and R$^7$ together form Q, wherein Q means γ'-CH=CH—CH=CR$^{18}$-δ', R$^8$ means H, Cl, Br, NO$_2$, OH, O—CH$_2$phenyl, CO$_2$H or methyl, R$^9$ means H or methyl, or R$^8$ and R$^9$ together form U, wherein U means ε'-CH=CH—CH=CH-η', and R$^{18}$ means H or OH, and the pharmaceutically acceptable salts thereof.

Highly preferred compounds according to the invention are those which are selected from among:
  9-chloro-4-(4-methoxyphenyl)-3-methyl-7-trifluoromethyl-3,4-dihydro-2H-pyrido[1,2-a]pyrimidine 2-carboxylic acid,
  9-chloro-4-(4-methoxyphenyl)-3-methyl-7-trifluoromethyl-3,4-dihydro-2H-pyrido[1,2-a]pyrimidine 2-carboxylic acid ethyl ester,
  7,9-dichloro-4-(3,4-dimethoxyphenyl)-3,4-dihydro-2H-pyrido[1,2-a]pyrimidine 2-carboxylic acid ethyl ester,
  7,9-dibromo-4-(3,4-dimethoxyphenyl)-3,4-dihydro-2H-pyrido[1,2-a]pyrimidine 2-carboxylic acid ethyl ester,
  4-(3,4-dimethoxyphenyl)-7-nitro-3,4-dihydro-2H-pyrido[1,2-a]pyrimidine 2-carboxylic acid ethyl ester,
  7,9-dichloro-4-(4-methoxyphenyl)-3,4-dihydro-2H-pyrido[1,2-a]pyrimidine 2-carboxylic acid ethyl ester,
  4-(4-methoxyphenyl)-7-nitro-3,4-dihydro-2H-pyrido[1,2-a]pyrimidine 2-carboxylic acid ethyl ester,
  7,9-dichloro-4-(3,4-dimethoxyphenyl)-3,4-dihydro-2H-pyrido[1,2-a]pyrimidine 2-carboxylic acid,
  7,9-dibromo-4-(3,4-dimethoxyphenyl)-6-methyl-3,4-dihydro-2H-pyrido[1,2-a]pyrimidine 2-carboxylic acid,
  4-(3,4-dimethoxyphenyl)-7-nitro-3,4-dihydro-2H-pyrido[1,2-a]pyrimidine 2-carboxylic acid,
  7,9-dichloro-4-(4-methoxyphenyl)-3,4-dihydro-2H-pyrido[1,2-a]pyrimidine 2-carboxylic acid,
  4-(4-methoxyphenyl)-7-nitro-3,4-dihydro-2H-pyrido[1,2-a]pyrimidine 2-carboxylic acid,
  7-bromo-4-(4-methoxyphenyl)-9-nitro-3,4-dihydro-2H-pyrido[1,2-a]pyrimidine 2-carboxylic acid, 7,9-dichloro-4-(3,4-dimethoxyphenyl)-2-(5-nitro-2-furanyl)-3,4-dihydro-2H-pyrido[1,2-a]pyrimidine, 7,9-dibromo-4-(3,4-dimethoxyphenyl)-2-(5-nitro-2-furanyl)-3,4-dihydro-2H-pyrido[1,2-a]pyrimidine, 4-(3,4-dimethoxyphenyl)-7-nitro-2-(5-nitro-2-furanyl)-3,4-dihydro-2H-pyrido[1,2-a]pyrimidine, 7,9-dichloro-4-(4-methoxyphenyl)-2-(5-nitro-2-furanyl)-3,4-dihydro-2H-pyrido[1,2-a]pyrimidine, 2-[7,9-dichloro-4-(2,4-dimethylphenyl)-3,4-dihydro-2H-pyrido[1,2-a]pyrimidine-2-yl]-cyclopropane carboxylic acid ethyl ester, 2-[9-chloro-4-(2,4-dimethylphenyl)-7-trifluoromethyl-3,4-dihydro-2H-pyrido[1,2-a]pyrimidine-2-yl]-cyclopropane carboxylic acid ethyl ester, 2-[7,9-dibromo-4-(3,4-dimethoxyphenyl)-3,4-dihydro-2H-pyrido[1,2-a]-2-pyrimidinyl]-cyclopropane carboxylic acid ethyl ester, 2-[7,9-dichloro-4-(4-methoxyphenyl)-3,4-dihydro-2H-pyrido[1,2-a]-2-pyrimidinyl]-cyclopropane carboxylic acid ethyl ester, 2-[7,9-dibromo-4-(4-methoxyphenyl)-3,4-dihydro-2H-pyrido[1,2-a]-2-pyrimidinyl]-cyclopropane carboxylic acid ethyl ester, 2-[9-chloro-4-(4-methoxyphenyl)-7-trifluoromethyl-3,4-dihydro-2H-pyrido[1,2-a]-2-pyrimidinyl]-cyclopropane carboxylic acid ethyl ester, 2-[4-(4-methoxyphenyl)-7-nitro-3,4-dihydro-2H-pyrido[1,2-a]-2-pyrimidinyl]-cyclopropane carboxylic acid ethyl ester, 4-(4-hydroxyphenyl)-3-methyl-7-nitro-3,4-dihydro-2H-pyrido[1,2-a]pyrimidine 2-carboxylic acid ethyl ester, 7,9-dichloro-4-phenylsulfanyl-3,4-dihydro-2H-pyrido[1,2-a]pyrimidine 2-carboxylic acid, 7-nitro-4-phenylsulfanyl-3,4-dihydro-2H-pyrido[1,2-a]pyrimidine 2-carboxylic acid, 7,9-dichloro-4-(4-hydroxy-3-methoxyphenyl)-3-methyl-3,4-dihydro-2H-pyrido[1,2-a]pyrimidine 2-carboxylic acid, 7,9-dibromo-4-(4-hydroxy-3-methoxyphenyl)-3-methyl-3,4-dihydro-2H-pyrido[1,2-a]pyrimidine 2-carboxylic acid, 7,9-dibromo-4-(4-hydroxy-3-methoxyphenyl)-3,6-dimethyl-3,4-dihydro-2H-pyrido[1,2-a]pyrimidine 2-carboxylic acid, 9-chloro-4-(4-hydroxy-3-methoxyphenyl)-3-methyl-7-trifluoromethyl-3,4-dihydro-2H-pyrido[1,2-a]pyrimidine 2-carboxylic acid, 7,9-dichloro-4-(4-methoxyphenyl)-3-methyl-3,4-dihydro-2H-pyrido[1,2-a]pyrimidine 2-carboxylic acid, 7,9-dibromo-4-(4-methoxyphenyl)-3-methyl-3,4-dihydro-2H-pyrido[1,2-a]pyrimidine 2-carboxylic acid ethyl ester, 7,9-dibromo-4-(4-methoxyphenyl)-3-methyl-3,4-dihydro-2H-pyrido[1,2-a]pyrimidine 2-carboxylic acid, 7,9-dibromo-4-(4-methoxyphenyl)-3,6-dimethyl-3,4-dihydro-2H-pyrido[1,2-a]pyrimidine 2-carboxylic acid, 9-chloro-4-(4-methoxyphenyl)-3-methyl-7-trifluoromethyl-3,4-dihydro-2H-pyrido[1,2-a]pyrimidine 2-carboxylic acid, 4-(4-methoxyphenyl)-3-methyl-7-nitro-3,4-dihydro-2H-pyrido[1,2-a]pyrimidine 2-carboxylic acid, 7-bromo-4-(4-methoxyphenyl)-3-methyl-9-nitro-3,4-dihydro-2H-pyrido[1,2-a]pyrimidine 2-carboxylic acid, 7,9-dichloro-4-(4-hydroxyphenyl)-3-methyl-3,4-dihydro-2H-pyrido[1,2-a]pyrimidine 2-carboxylic acid, 7,9-dibromo-4-(4-hydroxyphenyl)-3,6-dimethyl-3,4-dihydro-2H-pyrido[1,2-a]pyrimidine 2-carboxylic acid, 7,9-dichloro-4-(3,4-dimethoxyphenyl)-3,4-dihydro-2H-pyrido[1,2-a]pyrimidine 2-carboxylic acid, 7,9-dibromo-4-(3,4-dimethoxyphenyl)-3,4-dihydro-2H-pyrido[1,2-a]pyrimidine 2-carboxylic acid, 7,9-dibromo-4-(3,4-dimethoxyphenyl)-6-methyl-3,4-dihydro-2H-pyrido[1,2-a]pyrimidine 2-carboxylic acid, 9-chloro-4-(3,4-dimethoxyphenyl)-7-trifluoromethyl-3,4-dihydro-2H-pyrido[1,2-a]pyrimidine 2-carboxylic acid, 4-(3,4-dimethoxyphenyl)-7-nitro-3,4-dihydro-2H-pyrido[1,2-a]pyrimidine 2-carboxylic acid, 7,9-dichloro-4-(4-methoxyphenyl)-3,4-dihydro-2H-pyrido[1,2-a]pyrimidine 2-carboxylic acid, 7,9-dibromo-4-(4-methoxyphenyl)-3,4-dihydro-2H-pyrido[1,2-a]pyrimidine 2-carboxylic acid, 7,9-dibromo-4-(4-methoxyphenyl)-6-methyl-3,4-dihydro-2H-pyrido[1,2-a]pyrimidine 2-carboxylic acid, 9-chloro-4-(4-methoxyphenyl)-7-trifluoromethyl-3,4-dihydro-2H-pyrido[1,2-a]pyrimidine 2-carboxylic acid, 4-(4-methoxyphenyl)-7-nitro-3,4-dihydro-2H-pyrido[1,2-a]pyrimidine 2-carboxylic acid,

[7,9-dichloro-4-(4-hydroxy-3-methoxyphenyl)-3-methyl-3,4-dihydro-2H-pyrido[1,2-a]-2-pyrimidinyl]-phenylmethanone,

[7,9-dibromo-4-(4-hydroxy-3-methoxyphenyl)-3-methyl-3,4-dihydro-2H-pyrido[1,2-a]-2-pyrimidinyl]-phenylmethanone,

[7,9-dibromo-4-(4-hydroxy-3-methoxyphenyl)-3,6-dimethyl-3,4-dihydro-2H-pyrido[1,2-a]-2-pyrimidinyl]-phenylmethanone,

[4-(4-hydroxy-3-methoxyphenyl)-3-methyl-7-nitro-3,4-dihydro-2H-pyrido[1,2-a]-2-pyrimidinyl]-phenylmethanone,

[4-(4-methoxyphenyl)-3-methyl-7-nitro-3,4-dihydro-2H-pyrido[1,2-a]-2-pyrimidinyl]-phenylmethanone,

[7,9-dibromo-4-(4-hydroxyphenyl)-3,6-dimethyl-3,4-dihydro-2H-pyrido[1,2-a]-2-pyrimidinyl]-phenylmethanone,

[7,9-dichloro-4-(3,4-dimethoxyphenyl)-3,4-dihydro-2H-pyrido[1,2-a]-2-pyrimidinyl]-phenylmethanone,

[7,9-dibromo-4-(3,4-dimethoxyphenyl)-3,4-dihydro-2H-pyrido[1,2-a]-2-pyrimidinyl]-phenylmethanone,

[7,9-dibromo-4-(3,4-dimethoxyphenyl)-6-methyl-3,4-dihydro-2H-pyrido[1,2-a]-2-pyrimidinyl]-phenylmethanone,

[9-chloro-4-(3,4-dimethoxyphenyl)-7-trifluoromethyl-3,4-dihydro-2H-pyrido[1,2-a]-2-pyrimidinyl]-phenylmethanone,

[4-(3,4-dimethoxyphenyl)-7-nitro-3,4-dihydro-2H-pyrido[1,2-a]-2-pyrimidinyl]-phenylmethanone,

[4-(4-methoxyphenyl)-7-nitro-3,4-dihydro-2H-pyrido[1,2-a]-2-pyrimidinyl]-phenylmethanone, 2-(7,9-dichloro-2-cyclopropyl-3,4-dihydro-2H-pyrido[1,2-a]-4-pyrimidinyloxy)-ethanol, 2-(7,9-dibromo-2-cyclopropyl-3,4-dihydro-2H-pyrido[1,2-a]-4-pyrimidinyloxy)-ethanol, 2-(9-chloro-2-cyclopropyl-7-trifluoromethyl-3,4-dihydro-2H-pyrido[1,2-a]-4-pyrimidinyloxy)-ethanol, 2-(2-cyclopropyl-7-nitro-3,4-dihydro-2H-pyrido[1,2-a]-4-pyrimidinyloxy)-ethanol, 9-chloro-2-cyclopropyl-4-(3,4-dimethoxyphenyl)-7-trifluoromethyl-3,4-dihydro-2H-pyrido[1,2-a]pyrimidine, 7,9-dibromo-2-cyclopropyl-4-(4-methoxyphenyl)-3,4-dihydro-2H-pyrido[1,2-a]pyrimidine, 9-chloro-2-cyclopropyl-4-(4-methoxyphenyl)-7-trifluoromethyl-3,4-dihydro-2H-pyrido[1,2-a]pyrimidine, 2-cyclopropyl-4-(4-methoxyphenyl)-7-nitro-3,4-dihydro-2H-pyrido[1,2-a]pyrimidine,
2-(7,9-dichloro-2-cyclohexyl-3,4-dihydro-2H-pyrido[1,2-a]-4-pyrimidinyloxy)-ethanol,
2-(7,9-dibromo-2-cyclohexyl-3,4-dihydro-2H-pyrido[1,2-a]-4-pyrimidinyloxy)-ethanol,
2-(7,9-dibromo-2-cyclohexyl-6-methyl-3,4-dihydro-2H-pyrido[1,2-a]-4-pyrimidinyloxy)-ethanol,
2-(9-chloro-2-cyclohexyl-7-trifluoromethyl-3,4-dihydro-2H-pyrido[1,2-a]-4-pyrimidinyloxy)-ethanol,
2-(2-cyclohexyl-7-nitro-3,4-dihydro-2H-pyrido[1,2-a]-4-pyrimidinyloxy)-ethanol,
7,9-dichloro-2-cyclohexyl-4-(3,4-dimethoxyphenyl)-3,4-dihydro-2H-pyrido[1,2-a]pyrimidine,
7,9-dichloro-2-cyclohexyl-4-(4-methoxyphenyl)-3,4-dihydro-2H-pyrido[1,2-a]pyrimidine,
7,9-dibromo-2-cyclohexyl-4-(4-methoxyphenyl)-3,4-dihydro-2H-pyrido[1,2-a]pyrimidine,
9-chloro-2-cyclohexyl-4-(4-methoxyphenyl)-7-trifluoromethyl-3,4-dihydro-2H-pyrido[1,2-a]pyrimidine,
7,9-dibromo-4-(4-methoxyphenyl)-3-methyl-3,4-dihydro-2H-pyrido[1,2-a]pyrimidine 2-carboxylic acid ethyl ester,
7,9-dibromo-4-(4-methoxyphenyl)-3-methyl-3,4-dihydro-2H-pyrido[1,2-a]pyrimidine 2-carboxylic acid,
7,9-dibromo-4-(4-methoxyphenyl)-3-methyl-2-(5-nitro-2-furanyl)-3,4-dihydro-2H-pyrido[1,2-a]pyrimidine,
2-[7,9-dibromo-4-(4-methoxyphenyl)-3-methyl-3,4-dihydro-2H-pyrido[1,2-a]-2-pyrimidinyl]-cyclopropane carboxylic acid ethyl ester,
7,9-dibromo-4-(3,4-dimethoxyphenyl)-6-methyl-2-(5-nitro-2-furanyl)-3,4-dihydro-2H-pyrido[1,2-a]pyrimidine,
4-(4-methoxyphenyl)-7-nitro-2-(5-nitro-2-furanyl)-3,4-dihydro-2H-pyrido[1,2-a]pyrimidine,
2-[7,9-dibromo-4-(2,4-dimethylphenyl)-3,4-dihydro-2H-pyrido[1,2-a]-2-pyrimidinyl]-cyclopropane carboxylic acid ethyl ester,
2-[7,9-dibromo-4-(3,4-dimethoxyphenyl)-6-methyl-3,4-dihydro-2H-pyrido[1,2-a]-2-pyrimidinyl]-cyclopropane carboxylic acid ethyl ester,
2-[9-chloro-4-(3,4-dimethoxyphenyl)-7-trifluoromethyl-3,4-dihydro-2H-pyrido[1,2-a]-2-pyrimidinyl]-cyclopropane carboxylic acid ethyl ester,
2-[7,9-dibromo-4-(4-methoxyphenyl)-6-methyl-3,4-dihydro-2H-pyrido[1,2-a]-2-pyrimidinyl]-cyclopropane carboxylic acid ethyl ester,
2-[4-(4-fluorophenyl)-4-methyl-7-nitro-3,4-dihydro-2H-pyrido[1,2-a]-2-pyrimidinyl]-cyclopropane carboxylic acid ethyl ester,
9-benzyloxy-4-phenyl-2-pyridin-2-yl-3,4-dihydro-2H-pyrido[1,2-a]pyrimidine,
8-methyl-7-nitro-4-phenyl-2-pyridin-2-yl-3,4-dihydro-2H-pyrido[1,2-a]pyrimidine,
7,9-dichloro-4-phenyl-2-pyridin-2-yl-3,4-dihydro-2H-pyrido[1,2-a]pyrimidine,
9-chloro-4-phenyl-2-pyridin-2-yl-7-trifluoromethyl-3,4-dihydro-2H-pyrido[1,2-a]pyrimidine,
8-methyl-9-nitro-4-phenyl-2-pyridin-2-yl-3,4-dihydro-2H-pyrido[1,2-a]pyrimidine,
7-nitro-4-phenyl-2-pyridin-2-yl-3,4-dihydro-2H-pyrido[1,2-a]pyrimidine,
9-nitro-4-phenyl-2-pyridin-2-yl-3,4-dihydro-2H-pyrido[1,2-a]pyrimidine,
7-bromo-9-nitro-4-phenyl-2-pyridin-2-yl-3,4-dihydro-2H-pyrido[1,2-a]pyrimidine,
7,9-dibromo-6-methyl-4-phenyl-2-pyridin-2-yl-3,4-dihydro-2H-pyrido[1,2-a]pyrimidine,
7,9-dibromo-4-phenyl-2-pyridin-2-yl-3,4-dihydro-2H-pyrido[1,2-a]pyrimidine,
4-phenylsulfanyl-2-pyridin-2-yl-3,4-dihydro-2H-pyrido[1,2-a]pyrimidine-9-carboxylic acid,
7-methyl-4-phenylsulfanyl-2-pyridin-2-yl-3,4-dihydro-2H-pyrido[1,2-a]pyrimidine,
9-benzyloxy-4-phenylsulfanyl-2-pyridin-2-yl-3,4-dihydro-2H-pyrido[1,2-a]pyrimidine,
8-methyl-7-nitro-4-phenylsulfanyl-2-pyridin-2-yl-3,4-dihydro-2H-pyrido[1,2-a]pyrimidine,
6-chloro-9-nitro-4-phenylsulfanyl-2-pyridin-2-yl-3,4-dihydro-2H-pyrido[1,2-a]pyrimidine,
7,9-dichloro-4-phenylsulfanyl-2-pyridin-2-yl-3,4-dihydro-2H-pyrido[1,2-a]pyrimidine,
9-chloro-4-phenylsulfanyl-2-pyridin-2-yl-7-trifluoromethyl-3,4-dihydro-2H-pyrido[1,2-a]pyrimidine,
8-methyl-9-nitro-4-phenylsulfanyl-2-pyridin-2-yl-3,4-dihydro-2H-pyrido[1,2-a]pyrimidine,
7-nitro-4-phenylsulfanyl-2-pyridin-2-yl-3,4-dihydro-2H-pyrido[1,2-a]pyrimidine,
7-bromo-4-phenylsulfanyl-2-pyridin-2-yl-3,4-dihydro-2H-pyrido[1,2-a]pyrimidine,
9-nitro-4-phenylsulfanyl-2-pyridin-2-yl-3,4-dihydro-2H-pyrido[1,2-a]pyrimidine,
7-bromo-9-methyl-4-phenylsulfanyl-2-pyridin-2-yl-3,4-dihydro-2H-pyrido[1,2-a]pyrimidine,
4-phenylsulfanyl-2-pyridin-2-yl-3,4-dihydro-2H-pyrido[1,2-a]-9-pyrimidinol,
7-chloro-4-phenyisulfanyl-2-pyridin-2-yl-3,4-dihydro-2H-pyrido[1,2-a]pyrimidine,
4-phenylsulfanyl-6-propyl-2-pyridine-2-yl-3,4-dihydro-2H-pyrido[1,2-a]pyrimidine,
7,9-dibromo-6-methyl-4-phenylsulfanyl-2-pyridin-2-yl-3,4-dihydro-2H-pyridol[1,2-a]pyrimidine,
4-phenylsulfanyl-2-pyridin-2-yl-7-trifluoromethyl-3,4-dihydro-2H-pyrido[1,2-a]pyrimidine,
7,9-dibromo-4-phenylsulfanyl-2-pyridin-2-yl-3,4-dihydro-2H-pyrido[1,2-a]pyrimidine,
1-phenylsulfanyl-3-pyridin-2-yl-2,3-dihydro-1H-pyrimidine[1,2-a]-10-quinolinol,
2-methyl-6-pyridin-2-yl-7,10-methano-6a,7,10,10a-tetrahydro-6H-pyrido[1,2-a]quinazoline,
2,4-dichloro-6-pyridin-2-yl-7,10-methano-6a,7,10,10a-tetrahydro-6H-pyrido[1,2-a]quinazoline,
4-chloro-6-pyridin-2-yl-2-trifluoromethyl-7,10-methano-6a,7,10,10a-tetrahydro-6H-pyrido[1,2-a]quinazoline,
2-nitro-6-pyridin-2-yl-7,10-methano-6a,7,10,10a-tetrahydro-6H-pyrido[1,2-a]quinazoline,
4-nitro-6-pyridin-2-yl-7,10-methano-6a,7,10,10a-tetrahydro-6H-pyrido[1,2-a]quinazoline,
2-chloro-6-pyridin-2-yl-7,10-methano-6a,7,10,10a-tetrahydro-6H-pyrido[1,2-a]quinazoline,
1-propyl-6-pyridin-2-yl-7,10-methano-6a,7,10,10a-tetrahydro-6H-pyrido[1,2-a]quinazoline,
2,4-dibromo-1-methyl-6-pyridin-2-yl-7,10-methano-6a,7,10,10a-tetrahydro-6H-pyrido[1,2-a]quinazoline,
6-pyridin-2-yl-2-trifluoromethyl-7,10-methano-6a,7,10,10a-tetrahydro-6H-pyrido[1,2-a]quinazoline,
1,4-methano-5-pyridin-2-yl-1,4a,5,12c-tetrahydro-4H-6,12b-diaza-benzo[c]-12-phenathrenol,
1,4-methano-5-pyridin-2-yl-1,4a,5,12c-tetrahydro-4H-6,12b-diaza-benzo[c]phenathrene, and
6-pyridin-2-yl-7,10-methano-6a,7,10,10a-tetrahydro-6H-isoquino[2,1-a]quinazoline, and the pharmaceutically acceptable salts thereof.

The invention also relates to a process for the production of the compounds according to the invention of the general formula I

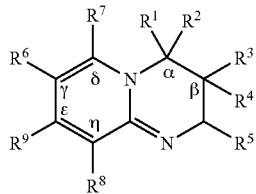

in which

R$^1$ and R$^2$ mutually independently mean H, OR$^{10}$, SH, SR$^{10}$, C$_{1-12}$ alkyl, wherein alkyl is linear or branched and is saturated or unsaturated and is unsubstituted or mono- or polysubstituted, C$_{3-8}$ cycloalkyl, wherein cycloalkyl is saturated or unsaturated and is unsubstituted or mono- or polysubstituted, aryl, wherein aryl is unsubstituted or mono- or polysubstituted, heteroaryl, wherein heteroaryl is unsubstituted or mono- or polysubstituted, (C$_{1-6}$ alkyl)aryl, wherein C$_{1-6}$ alkyl is linear or branched and is saturated or unsaturated and is unsubstituted or mono- or polysubstituted and aryl is unsubstituted or mono- or polysubstituted, or (C$_{1-6}$ alkyl)heteroaryl, wherein C$_{1-6}$ alkyl is linear or branched and is saturated or unsaturated and is unsubstituted or mono- or polysubstituted and heteroaryl is unsubstituted or mono- or polysubstituted, wherein one of R$^1$ and R$^2$ is H and the other of R$^1$ and R$^2$ is not H, providing that, if one of R$^1$ and R$^2$ means aryl, the other of R$^1$ and R$^2$ means H or C$_{1-12}$ alkyl, R$^3$ and R$^4$ mutually independently mean H, C$_{1-12}$ alkyl, wherein C$_{1-12}$ alkyl is linear or branched and is saturated or unsaturated and is unsubstituted or mono- or polysubstituted, C$_{3-8}$ cycloalkyl, wherein cycloalkyl is saturated or unsaturated and is unsubstituted or mono- or polysubstituted, aryl, wherein aryl is unsubstituted or mono- or polysubstituted, heteroaryl, wherein heteroaryl is unsubstituted or mono- or polysubstituted, (C$_{1-6}$ alkyl)aryl, wherein C$_{1-6}$ alkyl is linear or branched and is saturated or unsaturated and is unsubstituted or mono- or polysubstituted and aryl is unsubstituted or mono- or polysubstituted, or (C$_{1-6}$ alkyl)heteroaryl, wherein C$_{1-6}$ alkyl is linear or branched and is saturated or unsaturated and is unsubstituted or mono- or polysubstituted and heteroaryl is unsubstituted or mono- or polysubstituted, wherein at least one of R$^3$ and R$^4$ is H, or one of R$^1$ or R$^2$, together with one of R$^3$ or R$^4$, forms W, wherein W means α'-(CH$_2$)$_n$-β' where n=3, 4, 5, 6, 7, 8, 9 or 10, α'-CH=CH—CH$_2$-β', α'-CH=CH—CH$_2$—CH$_2$-β', α'-CH$_2$—CH=CH—CH$_2$-β', α'-CH$_2$—CH$_2$—CH=CH—CH$_2$—CH$_2$-β', α'-O—(CH$_2$)$_n$-β' where n=2, 3, 4, 5 or 6,

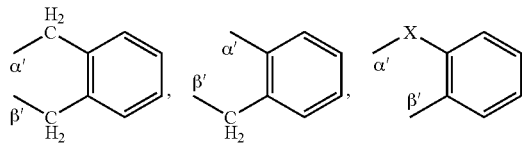

where X=CH$_2$, O or S,

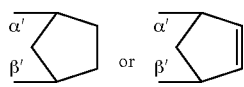

and the end of W marked α' is attached to the α carbon atom of the compound of the general formula I and the end of W marked β' is attached to the β carbon atom of the compound of the general formula I, the other of R$^1$ and R$^2$ is H or C$_{1-12}$ alkyl, wherein alkyl is linear or branched and is saturated or unsaturated and is unsubstituted or mono- or polysubstituted, and the other of R$^3$ and R$^4$ is H or C$_{1-12}$ alkyl, wherein alkyl is linear or branched and is saturated or unsaturated and is unsubstituted or mono- or polysubstituted, R$^5$ means C$_{1-12}$ alkyl, wherein C$_{1-12}$ alkyl is linear or branched and is saturated or unsaturated and is unsubstituted or mono- or polysubstituted, C$_{3-8}$ cycloalkyl, wherein cycloalkyl is saturated or unsaturated and is unsubstituted or mono- or polysubstituted, aryl, wherein aryl is unsubstituted or mono- or polysubstituted, heteroaryl, wherein heteroaryl is unsubstituted or mono- or polysubstituted, (C$_{1-6}$ alkyl)aryl, wherein C$_{1-6}$ alkyl is linear or branched and is saturated or unsaturated and is unsubstituted or mono- or polysubstituted and aryl is unsubstituted or mono- or polysubstituted, (C$_{1-6}$ alkyl)heteroaryl, wherein C$_{1-6}$ alkyl is linear or branched and is saturated or unsaturated and is unsubstituted or mono- or polysubstituted and heteroaryl is unsubstituted or mono- or polysubstituted, C(=O)R$^{11}$, CO$_2$H or CO$_2$R$^{12}$, R$^6$, R$^7$, R$^8$ and R$^9$ mutually independently mean H, F, Cl, Br, I, CN, NH$_2$, NH(C$_{1-6}$ alkyl), N(C$_{1-6}$ alkyl)$_2$, NH((C$_{1-6}$ alkyl)aryl), N((C$_{1-6}$ alkyl)aryl)$_2$, NHR$^{13}$, NO$_2$, OH, SH, O—C$_{1-8}$ alkyl or S(O)$_p$—C$_{1-8}$ alkyl, wherein alkyl is linear or branched and is saturated or unsaturated and is unsubstituted or mono- or polysubstituted and p is 0, 1 or 2, O-aryl or S(O)$_q$-aryl, wherein aryl is unsubstituted or mono- or polysubstituted and q is 0, 1 or 2, O—(C$_{1-6}$ alkyl)aryl or S(O)$_r$—(C$_{1-6}$ alkyl)aryl, wherein C$_{1-6}$ alkyl is linear or branched and is saturated or unsaturated and is unsubstituted or mono- or polysubstituted and aryl is unsubstituted or mono- or polysubstituted and r is 0, 1 or 2, CO$_2$H, C(=O)R$^{14}$, C$_{1-12}$ alkyl, wherein alkyl is linear or branched and is saturated or unsaturated and is unsubstituted or mono- or polysubstituted, CF$_3$, C$_{3-8}$ cycloalkyl, wherein cycloalkyl is saturated or unsaturated and is unsubstituted or mono- or polysubstituted, heterocyclyl, wherein heterocyclyl is 3-, 4-, 5-, 6- or 7-membered and is saturated or unsaturated and is unsubstituted or mono- or polysubstituted, aryl, wherein aryl is unsubstituted or mono- or polysubstituted, or heteroaryl, wherein heteroaryl is unsubstituted or mono- or polysubstituted, or R$^6$ and R$^7$ together form Q, wherein Q means γ'-CR$^{15}$=CR$^{16}$—CR$^{17}$=CR$^{18}$-δ', the end of Q marked γ' is attached to the γ carbon atom of the compound of the general formula I and the end of Q marked δ' is attached to the δ carbon atom of the compound of the general formula I, and R$^8$ and R$^9$ are defined as above, or R$^6$ and R$^9$ together form T, wherein T means γ'-CR$^{19}$=CR$^{20}$—CR$^{21}$=CR$^{22}$-ε' or γ'-N=CR$^{20}$—CR$^{21}$=N-ε', the end of T marked γ' is attached to the γ carbon atom of the compound of the general formula I and the end of T marked ε' is attached to the ε carbon atom of the compound of the general formula I, and R$^7$ and R$^8$ are defined as above, or R$^8$ and R$^9$ together form U, wherein U means η'-CR$^{19}$=CR$^{20}$—CR$^{21}$=CR$^{22}$-ε', the end of U marked η' is attached to the η carbon atom of the compound of the general formula I and the end of U marked ε' is attached to the ε carbon atom of the compound of the general formula I, and R$^6$ and R$^7$ are defined as above, R$^{10}$ means C$_{1-8}$ alkyl, wherein alkyl is linear or branched and is saturated or unsaturated and is unsubstituted or mono- or polysubstituted, C$_{3-8}$ cycloalkyl, wherein cycloalkyl is saturated or unsaturated and is unsubstituted or mono- or polysubstituted, aryl, wherein aryl is unsubstituted or mono- or polysubstituted, heteroaryl, wherein heteroaryl is unsubstituted or mono- or polysubstituted, ($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted, or ($C_{1-6}$ alkyl)heteroaryl, wherein $C_{1-6}$ alkyl is linear or branched and is saturated or unsaturated and is unsubstituted or mono- or polysubstituted and heteroaryl is unsubstituted or mono- or polysubstituted, $R^{11}$ means $NH_2$, $NH(C_{1-6}$ alkyl), $N(C_{1-6}$ alkyl$)_2$, $NH((C_{1-6}$ alkyl)aryl), $N((C_{1-6}$ alkyl)aryl$)_2$, $C_{1-8}$ alkyl, wherein alkyl is linear or branched and is saturated or unsaturated and is unsubstituted or mono- or polysubstituted, $C_{3-8}$ cycloalkyl, wherein cycloalkyl is saturated or unsaturated and is unsubstituted or mono- or polysubstituted, aryl, wherein aryl is unsubstituted or mono- or polysubstituted, heteroaryl, wherein heteroaryl is unsubstituted or mono- or polysubstituted, ($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted, or ($C_{1-6}$ alkyl)heteroaryl, wherein $C_{1-6}$ alkyl is linear or branched and is saturated or unsaturated and is unsubstituted or mono- or polysubstituted and heteroaryl is unsubstituted or mono- or polysubstituted, $R^{12}$ means $C_{1-8}$ alkyl, wherein alkyl is linear or branched and is saturated or unsaturated and is unsubstituted or mono- or polysubstituted, $C_{3-8}$ cycloalkyl, wherein cycloalkyl is saturated or unsaturated and is unsubstituted or mono- or polysubstituted, ($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted, $R^{13}$ means $C(=O)CH_3$, $C(=O)$phenyl, $C(=O)O$-t.-butyl (t-BOC) or any other conventional amino protective group, $R^{14}$ means H, $NH_2$, $NH(C_{1-6}$ alkyl), $N(C_{1-6}$ alkyl$)_2$, $NH((C_{1-6}$ alkyl)aryl), $N((C_{1-6}$ alkyl)aryl$)_2$, $C_{1-8}$ alkyl, wherein alkyl is linear or branched and is saturated or unsaturated and is unsubstituted or mono- or polysubstituted, $C_{3-8}$ cycloalkyl, wherein cycloalkyl is saturated or unsaturated and is unsubstituted or mono- or polysubstituted, aryl, wherein aryl is unsubstituted or mono- or polysubstituted, or ($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted, $OC_{1-8}$ alkyl, wherein alkyl is linear or branched and is saturated or unsaturated and is unsubstituted or mono- or polysubstituted, $OC_{3-8}$ cycloalkyl, wherein cycloalkyl is saturated or unsaturated and is unsubstituted or mono- or polysubstituted, Oaryl, wherein aryl is unsubstituted or mono- or polysubstituted, or O—($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted, $R^{15}$, $R^{16}$, $R^{17}$ and $R^{18}$ mutually independently mean H, F, Cl, Br, I, CN, OH, $C_{1-8}$ alkyl, wherein alkyl is linear or branched and is saturated or unsaturated and is unsubstituted or mono- or polysubstituted, or $CO_2H$, and $R^{19}$, $R^{20}$, $R^{21}$ and $R^{22}$ mutually independently mean H, F, Cl, Br, I, CN, OH, $C_{1-8}$ alkyl, wherein alkyl is linear or branched and is saturated or unsaturated and is unsubstituted or mono- or polysubstituted, or $CO_2H$, and the pharmaceutically acceptable salts thereof, wherein the process is characterized in that a heteroarylamine of the general formula II

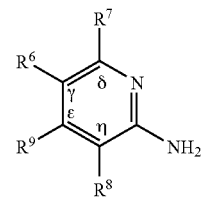

in which $R^6$ and $R^7$ are defined as above, providing that, if $R^6$ and $R^7$ form Q as defined above, the end of Q marked γ' is attached to the γ carbon atom of the heteroarylamine of the general formula II and the end of Q marked δ' is attached to the δ carbon atom of the heteroarylamine of the general formula II, that $R^6$ and $R^9$ form T as defined above, the end marked γ' is attached to the γ carbon atom of the heteroarylamine of the general formula II and the end marked ε' is attached to the ε carbon atom of the heteroarylamine of the general formula II, and that $R^8$ and $R^9$ form U as defined above, the end marked η' is attached to the η carbon atom of the heteroarylamine of the general formula II and the end marked ε' is attached to the ε carbon atom of the heteroarylamine of the general formula II, is reacted in the presence of an acid with an aldehyde of the general formula III

in which $R^5$ is defined as above, and an olefin of the general formula IV

in which $R^1$, $R^2$, $R^3$ and $R^4$ are defined as above, providing that, if one of the residues $R^1$ and $R^2$, together with one of residues $R^3$ and $R^4$, forms W, the end of W marked α' is attached to the α carbon atom of the olefin of the general formula IV and the end of W marked β' is attached to the β carbon atom of the olefin of the general formula IV.

The process according to the invention is preferably performed in a "single-vessel" reaction, in which one heteroarylamine of the general formula II, one aldehyde of the general formula III and one olefin of the general formula IV are simultaneously reacted together.

The process according to the invention may also be performed in semi- or fully automated form as a parallel synthesis of a group of compounds according to the invention of the general formula I.

The acid used may be an inorganic or organic protonic or Lewis acid. The reaction is preferably performed in the presence of an organic acid, for example acetic acid, trifluoroacetic acid or methanesulfonic acid, in particular trifluoroacetic acid.

The process according to the invention may be performed in any suitable solvent in which the reactants are adequately soluble. Preferred solvents are organic solvents, for example dichloromethane or in particular acetonitrile.

The production according to the invention of the compounds according to the invention of the general formula I conveniently proceeds at a temperature of 0 to 100° C., in particular at 15 to 40° C. The reaction time is preferably 15 minutes to 12 hours and may be tailored to the requirements of the particular case.

The heteroarylamines of the general formula II, the aldehydes of the general formula III and the olefins of the general formula IV used in the process according to the invention are commercially obtainable (from Acros, Geel; Avocado, Port of Heysham; Aldrich, Deisenhofen; Fluka, Seelze; Lancaster, Mülheim; Maybridge, Tintagel; Merck, Darmstadt; Sigma, Deisenhofen; TCI, Japan) or may be produced using processes generally known to a person of ordinary skills in the art.

The compounds according to the invention of the general formula I may be isolated both as a free base and as a salt. The free base of the compound of the general formula I is conventionally obtained after completion of the above-described process according to the invention and subsequent conventional working up. The base obtained in said manner may then be converted into the corresponding salt for example by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The salts formed comprise, inter alia, hydrochlorides, hydrobomides, phosphates, carbonates, hydrogencarbonates, formates, acetates, oxalates, succinates, tartrates, fumarates, citrates and glutamates. Formation of the particularly preferred hydrochloride may in particular also be achieved by combining the base, dissolved in a suitable solvent, with trimethylsilyl chloride (TMSCl).

Where the compounds of the general formula I are obtained in the production process according to the invention as racemates or as mixtures of the various enantiomers and/or diastereomers thereof, these mixtures may be separated using processes well known to the ordinarily skilled person in the art. Suitable methods are, inter alia, chromatographic separation processes, in particular liquid chromatography processes under standard or elevated pressure, preferably MPLC and HPLC processes, as well as fractional crystallization processes. Individual enantiomers may here in particular be separated from one another for example by means of HPLC on a chiral phase or by means of crystallization with chiral acids, such as (+)-tartaric acid, (−)-tartaric acid or (+)-10-camphorsulfonic acid.

The present invention also provides a substance library, which contains at least one compound of the general formula I

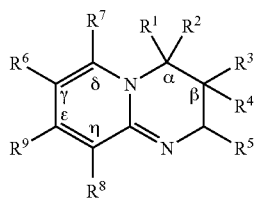

in which
$R^1$ and $R^2$ mutually independently mean H, $OR^{10}$, SH, $SR^{10}$, $C_{1-12}$ alkyl, wherein alkyl is linear or branched and is saturated or unsaturated and is unsubstituted or mono- or polysubstituted, $C_{3-8}$ cycloalkyl, wherein cycloalkyl is saturated or unsaturated and is unsubstituted or mono- or polysubstituted, aryl, wherein aryl is unsubstituted or mono- or polysubstituted, heteroaryl, wherein heteroaryl is unsubstituted or mono- or polysubstituted, ($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted, or ($C_{1-6}$ alkyl)heteroaryl, wherein $C_{1-6}$ alkyl is linear or branched and is saturated or unsaturated and is unsubstituted or mono- or polysubstituted and heteroaryl is unsubstituted or mono- or polysubstituted, wherein one of $R^1$ and $R^2$ is H and the other of $R^1$ and $R^2$ is not H, providing that, if one of $R^1$ and $R^2$ means aryl, the other of $R^1$ and $R^2$ means H or $C_{1-12}$ alkyl, $R^3$ and $R^4$ mutually independently mean H, $C_{1-12}$ alkyl, wherein $C_{1-12}$ alkyl is linear or branched and is saturated or unsaturated and is unsubstituted or mono- or polysubstituted, $C_{3-8}$ cycloalkyl, wherein cycloalkyl is saturated or unsaturated and is unsubstituted or mono- or polysubstituted, aryl, wherein aryl is unsubstituted or mono- or polysubstituted, heteroaryl, wherein heteroaryl is unsubstituted or mono- or polysubstituted, ($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted, or ($C_{1-6}$ alkyl)heteroaryl, wherein $C_{1-6}$ alkyl is linear or branched and is saturated or unsaturated and is unsubstituted or mono- or polysubstituted and heteroaryl is unsubstituted or mono- or polysubstituted, wherein at least one of $R^3$ and $R^4$ is H, or one of $R^1$ or $R^2$, together with one of $R^3$ or $R^4$, forms W, wherein W means α'-$(CH_2)_n$-β' where n=3, 4, 5, 6, 7, 8, 9 or 10, α'-CH=CH—$CH_2$-β', α'-CH=CH—$CH_2$—$CH_2$-β', α'-$CH_2$—CH=CH—$CH_2$-β', α'-$CH_2$—$CH_2$—CH=CH—$CH_2$—$CH_2$-β', α'-O—$(CH_2)_n$-β' where n=2, 3, 4, 5 or 6,

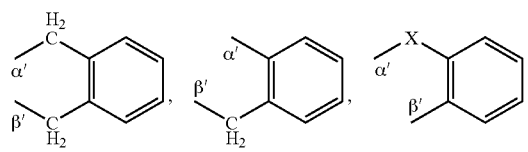

where X=$CH_2$, O or S,

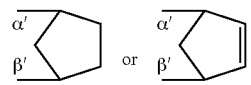

and the end of W marked α' is attached to the α carbon atom of the compound of the general formula I and the end of W marked β' is attached to the β carbon atom of the compound of the general formula I, the other of $R^1$ and $R^2$ is H or $C_{1-12}$ alkyl, wherein alkyl is linear or branched and is saturated or unsaturated and is unsubstituted or mono- or polysubstituted, and the other of $R^3$ and $R^4$ is H or $C_{1-12}$ alkyl, wherein alkyl is linear or branched and is saturated or unsaturated and is unsubstituted or mono- or polysubstituted, $R^5$ means $C_{1-12}$ alkyl, wherein $C_{1-12}$ alkyl is linear or branched and is saturated or unsaturated and is unsubstituted or mono- or polysubstituted, $C_{3-8}$ cycloalkyl, wherein cycloalkyl is saturated or unsaturated and is unsubstituted or mono- or polysubstituted, aryl, wherein aryl is unsubstituted or mono- or polysubstituted, heteroaryl, wherein heteroaryl is unsubstituted or mono- or polysubstituted, ($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted, ($C_{1-6}$ alkyl)heteroaryl, wherein $C_{1-6}$ alkyl is linear or branched and is saturated or unsaturated and is unsubstituted or mono- or polysubstituted and heteroaryl is unsubstituted or mono- or polysubstituted, C(=O)$R^{11}$, $CO_2H$ or $CO_2R^{12}$, $R^6$, $R^7$, $R^8$ and $R^9$ mutually independently mean H, F, Cl, Br, I, CN, $NH_2$, NH($C_{1-6}$ alkyl), N($C_{1-6}$ alkyl)$_2$, NH(($C_{1-6}$ alkyl)aryl), N(($C_{1-6}$ alkyl)aryl)$_2$, $NHR^{13}$, $NO_2$, OH, SH, O—$C_{1-8}$ alkyl or S(O)$_p$—$C_{1-8}$ alkyl, wherein alkyl is linear or branched and is saturated or unsaturated and is unsubstituted or mono- or polysubstituted and p is 0, 1 or 2, O-aryl or S(O)$_q$-aryl, wherein aryl is unsubstituted or mono- or polysubstituted and q is 0, 1 or 2, O—($C_{1-6}$ alkyl)aryl or S(O)$_r$—($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted and r is 0, 1 or 2, $CO_2H$, C(=O)$R^{14}$, $C_{1-12}$ alkyl, wherein alkyl is linear or branched and is saturated or unsaturated and is unsubstituted or mono- or polysubstituted, $CF_3$, $C_{3-8}$ cycloalkyl, wherein cycloalkyl is saturated or unsaturated and is unsubstituted or mono- or polysubstituted, heterocyclyl, wherein heterocyclyl is 3-, 4-, 5-, 6- or 7-membered and is saturated or unsaturated and is unsubstituted or mono- or polysubstituted, aryl, wherein aryl is unsubstituted or mono- or polysubstituted, or heteroaryl, wherein heteroaryl is unsubstituted or mono- or polysubstituted, or $R^6$ and $R^7$ together form Q, wherein Q means γ'-$CR^{15}$=$CR^{16}$—$CR^{17}$=$CR^{18}$-δ', the end of Q marked γ' is attached to the γ carbon atom of the compound of the general formula I and the end of Q marked δ' is attached to the δ carbon atom of the compound of the general formula I, and $R^8$ and $R^9$ are defined as above, or $R^6$ and $R^9$ together form T, wherein T means γ'-$CR^{19}$=$CR^{20}$—$CR^{21}$=$CR^{22}$-ε' or γ'-N=$CR^{20}$—$CR^{21}$=N-ε', the end of T marked γ' is attached to the γ carbon atom of the compound of the general formula I and the end of T marked ε' is attached to the ε carbon atom of the compound of the general formula I, and $R^7$ and $R^8$ are defined as above, or $R^8$ and $R^9$ together form U, wherein U means η'-$CR^{19}$=$CR^{20}$—$CR^{21}$=$CR^{22}$-ε', the end of U marked η' is attached to the η carbon atom of the compound of the general formula I and the end of U marked ε' is attached to the ε carbon atom of the compound of the general formula I, and $R^6$ and $R^7$ are defined as above, $R^{10}$ means $C_{1-8}$ alkyl, wherein alkyl is linear or branched and is saturated or unsaturated and is unsubstituted or mono- or polysubstituted, $C_{3-8}$ cycloalkyl, wherein cycloalkyl is saturated or unsaturated and is unsubstituted or mono- or polysubstituted, aryl, wherein aryl is unsubstituted or mono- or polysubstituted, heteroaryl, wherein heteroaryl is unsubstituted or mono- or polysubstituted, ($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted, or ($C_{1-6}$ alkyl)heteroaryl, wherein $C_{1-6}$ alkyl is linear or branched and is saturated or unsaturated and is unsubstituted or mono- or polysubstituted and heteroaryl is unsubstituted or mono- or polysubstituted, $R^{11}$ means $NH_2$, NH($C_{1-6}$ alkyl), N($C_{1-6}$ alkyl)$_2$, NH(($C_{1-6}$ alkyl)aryl), N(($C_{1-6}$ alkyl)aryl)$_2$, $C_{1-8}$ alkyl, wherein alkyl is linear or branched and is saturated or unsaturated and is unsubstituted or mono- or polysubstituted, $C_{3-8}$ cycloalkyl, wherein cycloalkyl is saturated or unsaturated and is unsubstituted or mono- or polysubstituted, aryl, wherein aryl is unsubstituted or mono- or polysubstituted, heteroaryl, wherein heteroaryl is unsubstituted or mono- or polysubstituted, ($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted, or ($C_{1-6}$ alkyl)heteroaryl, wherein $C_{1-6}$ alkyl is linear or branched and is saturated or unsaturated and is unsubstituted or mono- or polysubstituted and heteroaryl is unsubstituted or mono- or polysubstituted, $R^{12}$ means $C_{1-8}$ alkyl, wherein alkyl is linear or branched and is saturated or unsaturated and is unsubstituted or mono- or polysubstituted, $C_{3-8}$ cycloalkyl, wherein cycloalkyl is saturated or unsaturated and is unsubstituted or mono- or polysubstituted, ($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted, $R^{13}$ means C(=O)$CH_3$, C(=O)phenyl, C(=O)O-t.-butyl (t-BOC), $R^{14}$ means H, $NH_2$, NH($C_{1-6}$ alkyl), N($C_{1-6}$ alkyl)$_2$, NH(($C_{1-6}$ alkyl)aryl), N(($C_{1-6}$ alkyl)aryl)$_2$, $C_{1-8}$ alkyl, wherein alkyl is linear or branched and is saturated or unsaturated and is unsubstituted or mono- or polysubstituted, $C_{3-8}$ cycloalkyl, wherein cycloalkyl is saturated or unsaturated and is unsubstituted or mono- or polysubstituted, aryl, wherein aryl is unsubstituted or mono- or polysubstituted, or ($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted, $OC_{1-8}$ alkyl, wherein alkyl is linear or branched and is saturated or unsaturated and is unsubstituted or mono- or polysubstituted, $OC_{3-8}$ cycloalkyl, wherein cycloalkyl is saturated or unsaturated and is unsubstituted or mono- or polysubstituted, Oaryl, wherein aryl is unsubstituted or mono- or polysubstituted, or O—($C_{1-6}$ alkyl)aryl, wherein $C_{1-6}$ alkyl is linear or branched and is saturated or unsaturated and is unsubstituted or mono- or polysubstituted and aryl is unsubstituted or mono- or polysubstituted, $R^{15}$, $R^{16}$, $R^{17}$ and $R^{18}$ mutually independently mean H, F, Cl, Br, I, CN, OH, $C_{1-8}$ alkyl, wherein alkyl is linear or branched and is saturated or unsaturated and is unsubstituted or mono- or polysubstituted, or $CO_2H$, and $R^{19}$, $R^{20}$, $R^{21}$ and $R^{22}$ mutually independently mean H, F, Cl, Br, I, CN, OH, $C_{1-8}$ alkyl, wherein alkyl is linear or branched and is saturated or unsaturated and is unsubstituted or mono- or polysubstituted, or $CO_2H$.

The substance library according to the invention preferably contains at least 40 compounds, particularly preferably at least 80 and in particular at least 120 compounds of the general formula I as defined above.

For the purposes of the present invention, a "substance library" is taken to mean a group of compounds which are produced using the same process under identical or virtually identical reaction conditions while varying one or more reagents. Such a substance library may contain the members of the library both as individual pure compounds and as a mixture of said compounds. Using this substance library, it is possible, for example, to carry out automated medical screening in one or more in vitro screening processes.

The present invention furthermore also provides a pharmaceutical preparation or composition which comprises at least one of the above-defined compounds according to the invention of the general formula I or the pharmaceutically acceptable salts thereof. Compounds suitable for the pharmaceutical composition include 6-chloro-2-(4-nitrophenyl)-4-phenyl-3,4-dihydro-2H-pyrido[1,2-a]pyrimidine, 2-(4-nitrophenyl)-4-phenyl-3,4-dihydro-2H-pyrido[1,2-a] pyrimidine, 2-(2-nitrophenyl)-4-phenyl-3,4-dihydro-2H-pyrido[1,2-a]pyrimidine, 2-(4-nitrophenyl)-4-(4-tolyl)-3,4-dihydro-2H-pyrido[1,2-a]pyrimidine, 2-(4-chlorophenyl)-4-(4-totyl)-3,4-dihydro-2H-pyrido[1,2-a]pyrimidine, 4-ethoxy-2-phenyl-3,4-dihydro-2H-pyrido[1,2-a]pyrimidine, 4-ethoxy-2-(2-hydroxyphenyl)-3,4-dihydro-2H-pyrido[1,2-a]pyrimidine, 4-ethoxy-2-propyl-3,4-dihydro-2H-pyrido[1,2-a]pyrimidine, 4-propyl-2,3,3a,4,5,10a-hexahydro-2H-pyrido[1,2-a]furo[3,2-e]pyrimidine and/or 4-propyl-2,4,4a,5,6,11a-hexahydro-2H-pyrido[1,2-a]pyrano[3,2-e]pyrimidine.

These compounds may be present in the pharmaceutical preparation according to the invention not only as isomerically pure, in particular enantiomerically pure or diastereomerically pure, compounds but also as a racemic or nonracemic mixture. It is preferred for the pharmaceutical preparation to contain a pharmaceutically acceptable salt of the compounds according to the invention, in particular a hydrochloride.

The present invention also provides the use of at least one compound according to the invention of the general formula I, including the diastereomers or enantiomers thereof, also as racemates or an enantiomeric mixture in the form of the free base thereof or of a salt formed with a physiologically acceptable acid, in particular in the form of the hydrochloride salt, for the production of a pharmaceutical preparation the treatment of pain. The compounds according to the invention have proved to be analgesically active.

It has surprisingly been found that the compounds according to the invention of the general formula I are highly suitable for further indications, in particular for the treatment of urinary incontinence, pruritus, tinnitus and/or diarrhea. The present application accordingly also provides the use of at least one compound according to the invention of the general formula I, including a pharmaceutically acceptable salt for the production of a pharmaceutical preparation for the treatment of urinary incontinence, pruritus, tinnitus and/or diarrhea.

The present invention furthermore provides pharmaceutical compositions which contain at least one compound of the above-defined general formula I or of a pharmaceutically acceptable salt thereof and one or more pharmaceutical auxiliary substances.

The pharmaceutical preparations and pharmaceutical compositions according to the invention may be liquid, semi-solid or solid dosage forms and assume the form of and be administered as, for example, solutions for injection, drops, succi, syrups, sprays, suspensions, granules, tablets, pellets, transdermal therapeutic systems, capsules, dressings, suppositories, ointments, creams, lotions, gels, emulsions or aerosols and, depending upon the presentation, they contain, in addition to at least one compound according to the invention of the general formula I, pharmaceutical auxiliary substances, such as excipients, fillers, solvents, diluents, surface-active substances, dyes, preservatives, suspending agents, slip additives, lubricants, flavors and/or binders. These auxiliary substances may be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methylcellulose, carboxymethylcellulose, cellulose acetate, shellac, cetyl alcohol, polyvinylpyrrolidone, paraffins, waxes, natural and synthetic gums, gum arabic, alginates, dextran, saturated and unsaturated fatty acids, stearic acid, magnesium stearate, zinc stearate, glyceryl stearate, sodium lauryl sulfate, edible oils, sesame oil, coconut oil, peanut oil, soya oil, lecithin, sodium lactate, polyoxyethylene and polyoxypropylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talcum, kaolin, pectin, crospovidone, agar and bentonite.

The auxiliary substances and the quantities thereof which are to be used are selected depending on whether the pharmaceutical preparation is to be administered orally, subcutaneously, parenterally, intravenously, vaginally, pulmonally, intraperitoneally, transdermally, intramuscularly, nasally, buccally, rectally or topically, for example onto infections of the skin or mucous membranes and into the eyes. Preparations in the form of tablets, coated tablets, capsules, granules, drops, succi and syrups are, inter alia, suitable for oral administration, while solutions, suspensions, readily reconstitutible powders for inhalation and sprays are suitable for parenteral, topical and inhalatory administration. Compounds according to the invention of the general formula I in a depot in dissolved form or in a dressing, optionally with the addition of skin penetration promoters, are suitable percutaneous administration preparations. Rectally, transmucosally, parenterally, orally or percutaneously administrable formulations may release the compounds according to the invention of the general formula I in delayed manner.

The pharmaceutical preparations and pharmaceutical compositions according to the invention are produced using means, devices, methods and processes well known to an ordinarily skilled person from the art of pharmaceutical formulation, as are described, for example, in "Remington's Pharmaceutical Sciences", ed. A. R. Gennaro, 17th edition, Mack Publishing Company, Easton, Pa. (1985), in particular in part 8, sections 76 to 93.

Thus, for example, for a solid formulation such as a tablet, the active ingredient of the pharmaceutical preparation, i.e. a compound of the general formula I or a pharmaceutically acceptable salt thereof, may be granulated with a pharmaceutical excipient, for example conventional tablet ingredients, such as maize starch, lactose, sucrose, sorbitol, talcum, magnesium stearate, dicalcium phosphate or pharmaceutically acceptable gums, and pharmaceutical diluents, such as water, in order to form a solid composition which contains a compound according to the invention or a pharmaceutically acceptable salt thereof in homogeneously dispersed manner. Homogeneously dispersed is here taken to mean that the active ingredient is uniformly dispersed throughout the composition, such that the latter may straightforwardly be subdivided into unit dosage forms containing an equal amount of the active ingredient, such as tablets, pills or capsules. The solid composition is then subdivided into unit dosage forms. The tablets or pills of the pharmaceutical preparation according to the invention or of the pharmaceutical compositions according to the invention may also be coated or compounded in another manner in order to provide a dosage form with delayed release. Suitable coating compositions are, inter alia, polymeric acids and mixtures of polymeric acids with materials such as, for example shellac, cetyl alcohol and/or cellulose acetate.

The quantity of active substance to be administered to the patient varies and is a function of the weight, age and medical history of the patient, the mode of administration, the indication and the severity of the condition. Conventionally, at least one compound according to the invention of the general formula I is administered in a quantity of 0.1 to 5000 mg/kg, in particular of 1 to 500 mg/kg, preferably of 2 to 250 mg/kg body weight.

The purpose of the following Examples is to illustrate the present invention in greater detail.

EXAMPLES

The chemicals and solvents used were purchased from one of the following suppliers: Acros, Geel; Avocado, Port of Heysham; Aldrich, Deisenhofen; Fluka, Seelze; Lancaster, Mülheim; Maybridge, Tintagel; Merck, Darmstadt; Sigma, Deisenhofen; TCI, Japan; or were produced in accordance with processes generally known in the art.

Chromatographic purification was performed on an HPLC-RP-18 column from Macherey-Nagel; material NUCLEOSIL 100-3 $C_{18}$—HD, approx. 100 mm (VarioPrep), internal diameter 21 mm; mobile solvent water/methanol, gradient: 50–100% in approx. 18 min., flow rate: 10 ml/min; detection: UV, Beckman 168 PDA.

General Procedure, GP(Semi-Automated Synthesis)

A stirrer was placed in a round-bottomed glass tube (diameter 16 mm, length 125 mm) with a thread and the tube sealed using a screw lid with septum. The tube was placed in a stirring block, which had been adjusted to 20° C. The following reagents were then added in succession by pipette:

1 ml of a solution of trifluoroacetic acid, 0.1 M, and heteroarylamine component II, 0.1 M, in acetonitrile;
1 ml of a 0.11 M solution of the aldehyde III in acetonitrile;
1 ml of a 0.3 M solution of the olefin IV in acetonitrile.

The reaction mixture was stirred for 10 hours at 20° C. in one of the stirring blocks. The reaction solution was then filtered off. The tube was here rinsed twice with 1.5 ml portions of a 7.5% $NaHCO_3$ solution.

The rack containing the samples was placed manually on the working up unit. The reaction mixture was combined with 2 ml of ethyl acetate on a vortexer and shaken. The mixture was briefly centrifuged in the centrifuge to form a phase boundary. The phase boundary was detected optically and the organic phase removed by pipette. In the next step, the aqueous phase was again combined with 2 ml of ethyl acetate, shaken, centrifuged and the organic phase removed by pipette. The combined organic phases were dried over 2.4 g of $MgSO_4$ (pellets). The solvent was removed in a vacuum centrifuge.

Each sample was characterized by ESI-MS and/or NMR. Mass spectrometric investigation (ESI-MS) was carried out using a Finnegan LCQ Classic mass spectrometer. $^1$H-NMR investigations of the compounds according to the invention were carried out with a 300 MHz Bruker DPX Advance NMR spectrometer.

Examples 1–131 (see Table 1) were produced in accordance with the above general procedure. Examples 80 to 89 were worked by means of reversed-phase (RP) HPLC.

TABLE 1

| Example | Calculated mass | Actual mass | Compound |
| --- | --- | --- | --- |
| 1 | 400.78 | 401.2/403.2 | 9-chloro-4-(4-methyoxyphenyl)-3-methyl-7-trifluoromethyl-3,4-dihydro-2H-pyrido[1,2-a]pyrimidine 2-carboxylic acid |
| 2 | 428.83 | 429.2/430.1 | 9-chloro-4-(4-methyoxyphenyl)-3-methyl-7-trifluoromethyl-3,4-dihydro-2H-pyridol[1,2-a]pyrimidine 2-carboxylic acid ethyl ester |
| 3 | 411.28 | 411.1/413.1 | 7,9-dichloro-4-(3,4-dimethoxyphenyl)-3,4-dihydro-2H-pyrido[1,2-a]pyrimidine 2-carboxylic acid ethyl ester |
| 4 | 500.19 | 499.1/501.0/503.0 | 7,9-dibromo-4-(3,4-dimethoxyphenyl)-3,4-dihydro-2H-pyrido[1,2-a]pyrimidine 2-carboxylic acid ethyl ester |
| 5 | 387.39 | 388.2 | 4-(3,4-dimethoxyphenyl)-7-nitro-3,4-dihydro-2H-pyrido[1,2-a]pyrimidine 2-carboxylic acid ethyl ester |
| 6 | 381.25 | 381.1/383.0 | 7,9-dichloro-4-(4-methyoxyphenyl)-3,4-dihydro-2H-pyridol[1,2-a]pyrimidine 2-carboxylic acid ethyl ester |
| 7 | 357.36 | 358.2 | 4-(4-methyoxyphenyl)-7-nitro-3,4-dihydro-2H-pyridol[1,2-a]pyrimidine 2-carboxylic acid ethyl ester |
| 8 | 383.23 | 383.2/385.0 | 7,9-dichloro-4-(3,4-dimethoxyphenyl)-3,4-dihydro-2H-pyrido[1,2-a]pyrimidine 2-carboxylic acid |
| 9 | 486.16 | 485.1/487.0/488.9 | 7,9-dibromo-4-(3,4-dimethoxyphenyl)-6-methyl-3,4-dihydro-2H-pyrido[1,2-a]pyrimidine 2-carboxylic acid |
| 10 | 359.33 | 360.1 | 4-(3,4-dimethyoxyphenyl)-7-nitro-3,4-dihydro-2H-pyridol[1,2-a]pyrimidine 2-carboxylic acid |
| 11 | 353.2 | 353.1/355.0 | 7,9-dichloro-4-(4-methyoxyphenyl)-3,4-dihydro-2H-pyrido[1,2-a]pyrimidine 2-carboxylic acid |
| 12 | 329.31 | 330.1 | 4-(4-methoxyphenyl)-7-nitro-3,4-dihydro-2H-pyrido[1,2-a]pyrimidine 2-carboxylic acid |
| 13 | 408.21 | 408.1/410.1 | 7-bromo-4-(4-methyoxyphenyl)-9-nitro-3,4-dihydro-2H-pyrido[1,2-a]pyrimidine 2-carboxylic acid |
| 14 | 450.27 | 450.2/452.1 | 7,9-dichloro-4-(3,4-dimethoxyphenyl)-2-(5-nitro-2-furanyl)-3,4-dihydro-2H-pyrido[1,2-a]pyrimidine |
| 15 | 539.18 | 538.1/540.1/542.0 | 7,9-dibromo-4-(3,4-dimethoxyphenyl)-2-(5-nitro-2-furanyl)-3,4-dihydro-2H-pyrido[1,2-a]pyrimidine |
| 16 | 426.38 | 427.2 | 4-(3,4-dimethoxyphenyl)-7-nitro-2-(5-nitro-2-furanyl)-3,4-dihydro-2H-pyrido[1,2-a]pyrimidine |
| 17 | 420.25 | 420.2/422.1 | 7,9-dichloro-4-(4-methyoxyphenyl)-2-(5-nitro-2-furanyl)-3,4-dihydro-2H-pyrido[1,2-a]pyrimidine |

TABLE 1-continued

| Example | Calculated mass | Actual mass | Compound |
|---|---|---|---|
| 18 | 419.35 | 419.3/421.1 | 2-[7,9-dichloro-4-(2,4-dimethylphenyl)-3,4-dihydro-2H-pyrido[1,2-a]-2-pyrimidinyl]-cyclopropane carboxylic acid ethyl ester |
| 19 | 452.9 | 453.3 | 2-[9-chloro-4-(2,4-dimethylphenyl)-7-trifluoromethyl-3,4-dihydro-2H-pyrido[1,2-a]-2-pyrimidinyl]-cyclopropane carboxylic acid ethyl ester |
| 20 | 540.26 | 539.3/541.1/543.1 | 2-[7,9-dibromo-4-(3,4-dimethoxyphenyl)-3,4-dihydro-2H-pyrido[1,2-a]-2-pyrimidinyl]-cyclopropane carboxylic acid ethyl ester |
| 21 | 421.32 | 421.1/423.1 | 2-[7,9-dichloro-4-(4-methoxyphenyl)-3,4-dihydro-2H-pyrido[1,2-a]-2-pyrimidinyl]-cyclopropane carboxylic acid ethyl ester |
| 22 | 510.23 | 509.1/511.0/513.0 | 2-[7,9-dibromo-4-(4-methoxyphenyl)-3,4-dihydro-2H-pyrido[1,2-a]-2-pyrimidinyl]-cyclopropane carboxylic acid ethyl ester |
| 23 | 454.87 | 455.2/456.0/457.1 | 2-[9-chloro-4-(4-methoxyphenyl)-7-trifluoromethyl-3,4-dihydro-2H-pyrido[1,2-a]-2-pyrimidinyl]-cyclopropane carboxylic acid ethyl ester |
| 24 | 397.43 | 398.2 | 2-[4-(4-methoxyphenyl)-7-nitro-3,4-dihydro-2H-pyrido[1,2-a]-2-pyrimidinyl]-cyclopropane carboxylic acid ethyl ester |
| 25 | 357.36 | 358.2 | 4-(4-hydroxyphenyl)-3-methyl-7-nitro-3,4-dihydro-2H-pyrido[1,2-a]pyrimidine 2-carboxylic acid ethyl ester |
| 26 | 355.24 | 355.1/357.0 | 7,9-dichloro-4-phenylsulfanyl-3,4-dihydro-2H-pyrido[1,2-a]pyrimidine 2-carboxylic acid |
| 27 | 331.34 | 332.1 | 7-nitro-4-phenylsulfanyl-3,4-dihydro-2H-pyrido[1,2-a]pyrimidine 2-carboxylic acid |
| 28 | 383.23 | 383.1/385.1 | 7,9-dichloro-4-(4-hydroxy-3-methyoxyphenyl)-3-methyl-3,4-dihydro-2H-pyrido[1,2-a]pyrimidine 2-carboxylic acid |
| 29 | 472.14 | 471.0/473.0/475.0 | 7,9-dibromo-4-(4-hydroxy-3-methoxyphenyl)-3-methyl-3,4-dihydro-2H-pyrido[1,2-a]pyrimidine 2-carboxylic acid |
| 30 | 486.16 | 485.0/487.0/488.9 | 7,9-dibromo-4-(4-hydroxy-3-methoxyphenyl)-3,6-dimethyl-34-dihydro-2H-pyrido[1,2-a]pyrimidine 2-carboxylic acid |
| 31 | 416.78 | 417.1/419.1 | 9-chloro-4-(4-hydroxy-3-methoxyphenyl)-3-methyl-7-trifluoromethyl-3,4-dihydro-2H-pyrido[1,2-a]pyrimidine 2-carboxylic acid |
| 32 | 367.23 | 367.1/369.1 | 7,9-dichloro-4-(4-methoxyphenyl)-3-methyl-3,4-dihydro-2H-pyrido[1,2-a]pyrimidine 2-carboxylic acid |
| 33 | 456.14 | 455.0/457.0/459.0 | 7,9-dibromo-4-(4-methoxyphenyl)-3-methyl-3,4-dihydro-2H-pyrido[1,2-a]pyrimidine 2-carboxylic acid |
| 34 | 470.17 | 469.0/471.0/472.9 | 7,9-dibromo-4-(4-methoxyphenyl)-3,6-dimethyl-3,4-dihydro-2H-pyrido[1,2-a]pyrimidine 2-carboxylic acid |
| 35 | 400.78 | 401.1/403.1 | 9-chloro-4-(4-methoxyphenyl)-3-methyl-7-trifluoromethyl-3,4-dihydro-2H-pyrido[1,2-a]pyrimidine 2-carboxylic acid |
| 36 | 343.33 | 344.2 | 4-(4-methoxyphenyl)-3-methyl-7-nitro-3,4-dihydro-2H-pyrido[1,2-a]pyrimidine 2-carboxylic acid |
| 37 | 422.23 | 422.1/424.0 | 7-bromo-4-(4-methoxyphenyl)-3-methyl-9-nitro-34-dihydro-2H-pyrido[1,2-a]pyrimidine 2-carboxylic acid |
| 38 | 353.2 | 353.1/355.1 | 7,9-dichloro-4-(4-hydroxyphenyl)-methyl-3,4-dihydro-2H-pyrido[1,2-a]pyrimidine 2-carboxylic acid |
| 39 | 456.14 | 455.0/457.0/459.0 | 7,9-dibromo-4-(4-hydroxyphenyl)-3,6-dimethyl-3,4-dihydro-2H-pyrido[1,2-a]pyrimidine 2-carboxylic acid |
| 40 | 383.23 | 383.1/385.1 | 7,9-dichloro-4-(3,4-dimethoxyphenyl)-3,4-dihydro-2H-pyrido[1,2-a]pyrimidine 2-carboxylic acid |
| 41 | 472.14 | 471.0/473.0/475.0 | 7,9-dibromo-4-(3,4-dimethoxyphenyl)-3,4-dihydro-2H-pyrido[1,2-a]pyrimidine 2-carboxylic acid |
| 42 | 486.16 | 485.0/487.0/489.0 | 7,9-dibromo-4-(3,4-dimethoxyphenyl)-6-methyl-3,4-dihydro-2H-pyrido[1,2-a]pyrimidine 2-carboxylic acid |
| 43 | 416.78 | 417.1 | 9-chloro-4-(3,4-dimethoxyphenyl)-7-trifluoromethyl-3,4-dihydro-2H-pyrido[1,2-a]pyrimidine 2-carboxylic acid |
| 44 | 359.33 | 360.2 | 4-(3,4-dimethoxyphenyl)-7-nitro-3,4-dihydro-2H-pyrido[1,2-a]pyrimidine 2-carboxylic acid |
| 45 | 285.3 | 286.2 | 4-(4-methoxyphenyl)-3,4-dihydro-2H-pyrazine[1,2-a]pyrimidine 2-carboxylic acid |
| 46 | 353.2 | 353.1/355.1 | 7,9-dichloro-4-(4-methoxyphenyl)-3,4-dihydro-2H-pyrido[1,2-a]pyrimidine 2-carboxylic acid |
| 47 | 442.11 | 441.0/443.0/445.0 | 7,9-dibromo-4-(4-methoxyphenyl)-3,4-dihydro-2H-pyrido[1,2-a]pyrimidine 2-carboxylic acid |
| 48 | 456.14 | 455.0/457.0/459.0 | 7,9-dibromo-4-(4-methoxyphenyl)-6-methyl-3,4-dihydro-2H-pyrido[1,2-a]pyrimidine 2-carboxylic acid |
| 49 | 386.75 | 387.1 | 9-chloro-4-(4-methoxyphenyl)-7-trifluoromethyl-3,4-dihydro-2H-pyrido[1,2-a]pyrimidine 2-carboxylic acid |
| 50 | 329.31 | 330.1 | 4-(4-methoxyphenyl)-7-nitro-3,4-dihydro-2H-pyrido[1,2-a]pyrimidine 2-carboxylic acid |
| 51 | 443.32 | 441.2/443.1/445.1 | [7,9-dichloro-4-(hydroxy-3-methoxyphenyl)-3-methyl-3,4-dihydro-2H-pyrido[1,2-a]-2-pyrimidinyl]-phenylmethanone |

TABLE 1-continued

| Example | Calculated mass | Actual mass | Compound |
|---|---|---|---|
| 52 | 532.24 | 533.0 | [7,9-dibromo-4-(4-hydroxy-3-methoxyphenyl)-3-methyl-3,4-dihydro-2H-pyrido[1,2-a9 -2-pyrimidinyl]-phenylmethanone |
| 53 | 546.26 | 545.0/547.0/549.0 | [7,9-dibromo-4-(4-hydroxy-3-methoxyphenyl)-3,6-dimethyl-3,4-dihydro-2H-pyrido[1,2-a]-2-pyrimidinyl]-phenylmethanone |
| 54 | 419.43 | 420.2 | [4-(4-hydroxy-3-methoxyphenyl)-3-methyl-7-nitro-3,4-dihydro-2H-pyrido[1,2-a]-2-pyrimidinyl]-phenylmethanone |
| 55 | 403.43 | 404.2 | [4-(4-methoxyphenyl)-3-methyl-7-nitro-3,4-dihydro-2H-pyrido[1,2-a]-2-pyrimidinyl]-phenylmethanone |
| 56 | 516.24 | 515.0/517.0/519.0 | [7,9-dibromo-4-(4-hydroxyphenyl)-3,6-dimethyl-3,4-dihydro-2H-pyrido[1,2-a]-2-pyrimidinyl]-phenylmethanone |
| 57 | 443.32 | 443.1/445.1 | [7,9-dichloro-4-(3,4-dimethoxyphenyl)-3,4-dihydro-2H-pyrido[1,2-a]-2-pyrimidinyl]-phenylmethanone |
| 58 | 532.24 | 531.1/533.1 | [7,9-dibromo-4-(3,4-dimethoxyphenyl)-3,4-dihydro-2H-pyrido[1,2-a]-2-pyrimidinyl]-phenylmethanone |
| 59 | 546.26 | 545.1/547.0 | [7,9-dibromo-4-(3,4-dimethoxyphenyl)-6-methyl-3,4-dihydro-2H-pyrido[1,2-a]-2-pyrimidinyl]-phenylmethanone |
| 60 | 476.88 | 477.1 | [9-chloro-4-(3,4-dimethoxyphenyl)-7-trifluoromethyl-3,4-dihydro-2H-pyrido[1,2-a]-2-pyrimidinyl]-phenylmethanone |
| 61 | 419.43 | 420.2 | [4-(3,4-dimethoxyphenyl)-7-nitro-3,4-dihydro-2H-pyrido[1,2-a]-2-pyrimidinyl]-phenylmethanone |
| 62 | 389.41 | 390.2 | [4-(4-methoxyphenyl)-7-nitro-3,4-dihydro-2H-pyrido[1,2-a]-2-pyrimidinyl]-phenylmethanone |
| 63 | 303.18 | 303.1/305.1 | 2-(7,9-dichloro-2-cyclopropyl-3,4-dihydro-2H-pyrido[1,2-a]-4-pyrimidinyloxy)-ethanol |
| 64 | 392.1 | 391.0/393.0/395.0 | 2-(7,9-dibromo-2-cyclopropyl-3,4-dihydro-2H-pyrido[1,2-a]-4-pyrimidinyloxy)-ethanol |
| 65 | 336.74 | 337.1/339.1 | 2-(9-chloro-2-cyclopropyl-7-trifluoromethyl-3,4-dihydro-2H-pyrido[1,2-a]-4-pyrimidinyloxy)-ethanol |
| 66 | 279.29 | 280.1 | 2-(2-cyclopropyl-7-nitro-3,4-dihydro-2H-pyrido[1,2-a]-4-pyrimidinyloxy)-ethanol |
| 67 | 412.83 | 413.1 | 9-chloro-2-cyclopropyl-4-(3,4-dimethoxyphenyl)-7-trifluoromethyl-3,4-dihydro-2H-pyrido[1,2-a]pyrimidine |
| 68 | 438.17 | 439.0 | 7,9-dibromo-2-cyclopropyl-4-(4-methoxyphenyl)-3,4-dihydro-2H-pyrido[1,2-a]pyrimidine |
| 69 | 382.81 | 383.1/385.1 | 9-chloro-2-cyclopropyl-4-(4-methoxyphenyl)-7-trifluoromethyl-3,4-dihydro-2H-pyrido[1,2-a]pyrimidine |
| 70 | 325.36 | 326.2 | 2-cyclopropyl-4-(4-methoxyphenyl)-7-nitro-3,4-dihydro-2H-pyrido[1,2-a]pyrimidine |
| 71 | 345.26 | 345.1/347.1 | 2-(7,9-dichloro-2-cyclohexyl-3,4-dihydro-2H-pyrido[1,2-a]-4-pyrimidinyloxy)-ethanol |
| 72 | 434.18 | 433.1/435.1/437.0 | 2-(7,9-dibromo-2-cyclohexyl-3,4-dihydro-2H-pyrido[1,2-a]-4-pyrimidinyloxy)-ethanol |
| 73 | 448.2 | 447.1/449.0/451.0 | 2-(7,9-dibromo-2-cyclohexyl-6-methyl-3,4-dihydro-2H-pyrido[1,2-a]-4-pyrimidinyloxy)-ethanol |
| 74 | 378.82 | 379.2/381.2 | 2-(9-chloro-2-cyclohexyl-7-trifluoromethyl-3,4-dihydro-2H-pyrido[1,2-a]-4-pyrimidinyloxy)-ethanol |
| 75 | 321.37 | 322.2 | 2-(2-cyclohexyl-7-nitro-3,4-dihydro-2H-pyrido[1,2-a]-4-pyrimidinyloxy)-ethanol |
| 76 | 421.36 | 421.1/423.1 | 7,9-dichloro-2-cyclohexyl-4-(3,4-dimethoxyphenyl)-3,4-dihydro-2H-pyrido[1,2-a]pyrimidine |
| 77 | 391.34 | 391.1/393.1 | 7,9-dichloro-2-cyclohexyl-4-(4-methoxyphenyl)-3,4-dihydro-2H-pyrido[1,2-a]pyrimidine |
| 78 | 480.25 | 479.1/481.1/483.0 | 7,9-dibromo-2-cyclohexyl-4-(4-methoxyphenyl)-3,4-dihydro-2H-pyrido[1,2-a]pyrimidine |
| 79 | 424.89 | 425.2/427.2 | 9-chloro-2-cyclohexyl-4-(4-methoxyphenyl)-7-trifluoromethyl-3,4-dihydro-2H-pyrido[1,2-a]pyrimidine |
| 80 | 484.19 | 485.0/487.0 | 7,9-dibromo-4-(4-methoxyphenyl)-3-methyl-3,4-dihydro-2H-pyrido[1,2-a]pyrimidine 2-carboxylic acid ethyl ester |
| 81 | 456.14 | 457.4/459.5 | 7,9-dibromo-4-(4-methoxyphenyl)-3-methyl-3,4-dihydro-2H-pyrido[1,2-a]pyrimidine 2-carboxylic acid |
| 82 | 523.19 | 522.4/524.3/526.2 | 7,9-dibromo-4-(4-methoxyphenyl)-3-methyl-2-(5-nitro-2-furanyl)-3,4-dihydro-2H-pyrido[1,2-a]pyrimidine |
| 83 | 524.26 | 525.2 | 2-[7,9-dibromo-4-(4-methoxyphenyl)-3-methyl-3,4-dihydro-2H-pyrido[1,2-a]-2-pyrimidinyl]-cyclopropane carboxylic acid ethyl ester |
| 84 | 553.21 | 554.2/555.2/556.2 | 7,9-dibromo-4-(3,4-dimethoxyphenyl)-6-methyl-2-(5-nitro-2-furanyl)-3,4-dihydro-2H-pyrido[1,2-a]pyrimidine |
| 85 | 396.35 | 397.1 | 4-(4-methoxyphenyl)-7-nitro-2-(5-nitro-2-furanyl)3,4-dihydro-2H-pyrido[1,2-a]pyrimidine |
| 86 | 508.26 | 509.1 | 2-[7,9-dibromo-4-(2,4-dimethylphenyl)-3,4-dihydro-2H-pyrido[1,2-a]-2-pyrimidinyl]-cyclopropane carboxylic acid ethyl ester |
| 87 | 554.28 | 553.2/555.1/557.1 | 2-[7,9-dibromo-4-(3,4-dimethoxyphenyl)-6-methyl-3,4-dihydro-2H-pyrido]1,2-a]-2-pyrimidinyl]-cyclopropane carboxylic acid ethyl ester |

TABLE 1-continued

| Example | Calculated mass | Actual mass | Compound |
|---|---|---|---|
| 88 | 484.9 | 485.5 | 2-[9-chloro-4-(3,4-dimethoxyphenyl)-7-trifluoromethyl-3,4-dihydro-2H-pyrido[1,2-a]-2-pyrimidinyl]-cyclopropane carboxylic acid ethyl ester |
| 89 | 524.26 | 525.1/527.2 | 2-[7,9-dibromo-4-(4-methoxyphenyl)-6-methyl-3,4-dihydro-2H-pyrido[1,2-a]-2-pyrimidinyl]-cyclopropane carboxylic acid ethyl ester |
| 90 | 399.42 | 400.2 | 2-[4-(4-fluorophenyl)-4-methyl-7-nitro-3,4-dihydro-2H-pyrido[1,2-a]-2-pyrimidinyl]-cyclopropane carboxylic acid ethyl ester |
| 91 | 393.51 | 291.3 (M+H–Obenzyl) | 9-benzyloxy-4-phenyl-2-pyridin-2-yl-3,4-dihydro-2H-pyrido[1,2-a]pyrimidine |
| 92 | 346.41 | 347.3 | 8-methyl-7-nitro-4-phenyl-2-pyridin-2-yl-3,4-dihydro-2H-pyrido[1,2-a]pyrimidine |
| 93 | 356.28 | 356.2/358.2 | 7,9-dichloro-4-phenyl-2-pyridin-2-yl-3,4-dihydro-2H-pyrido[1,2-a]pyrimidine |
| 94 | 389.83 | 390.3/392.2 | 9-chloro-4-phenyl-2-pyridin-2-yl-7-trifluoromethyl-3,4-dihydro-2H-pyrido[1,2-a]pyrimidine |
| 95 | 346.41 | 347.1 | 8-methyl-9-nitro-4-phenyl-2-pyridin-2-yl-3,4-dihydro-2H-pyrido[1,2-a]pyrimidine |
| 96 | 332.38 | 333.2 | 7-nitro-4-phenyl-2-pyridin-2-yl-3,4-dihydro-2H-pyrido[1,2-a]pyrimidine |
| 97 | 332.38 | 333.2 | 9-nitro-4-phenyl-2-pyridin-2-yl-3,4-dihydro-2H-pyrido[1,2-a]pyrimidine |
| 98 | 411.28 | 413.1/416.2 | 7-bromo-9-nitro-4-phenyl-2-pyridin-2-yl-3,4-dihydro-2H-pyrido[1,2-a]pyrimidine |
| 99 | 459.2 | 458.1/460.0/462.0 | 7,9-dibromo-6-methyl-4-phenyl-2-pyridin-2-yl-3,4-dihydro-2H-pyrido[1,2-a]pyrimidine |
| 100 | 445.18 | 444.2/446.1/448.0 | 7,8-dibromo-4-phenyl-2-pyridin-2-yl-3,4-dihydro-2H-pyrido[1,2-a]pyrimidine |
| 101 | 363.44 | 364.2 | 4-phenylsulfanyl-2-pyridin-2-yl-3,4-dihydro-2H-pyrido[1,2-a]pyrimidine-9-carboxylic acid |
| 102 | 333.45 | 334.2 | 7-methyl-4-phenylsulfanyl-2-pyridin-2-yl-3,4-dihydro-2H-pyrido[1,2-a]pyrimidine |
| 103 | 425.55 | 426.2 | 9-benzyloxy-4-phenylsulfanyl-2-pyridin-2-yl-3,4-dihydro-2H-pyrido[1,2-a]pyrimidine |
| 104 | 378.45 | 379.2 | 8-methyl-7-nitro-4-phenylsulfanyl-2-pyridin-2-yl-3,4-dihydro-2H-pyrido[1,2-a]pyrimidine |
| 105 | 398.87 | 399.1/400.0 | 6-chloro-9-nitro-4-phenylsulfanyl-2-pyridin-2-yl-3,4-dihydro-2H-pyrido[1,2-a]pyrimidine |
| 106 | 388.32 | 388.2/390.1 | 7,9-dichloro-4-phenylsulfanyl-2-pyridin-2-yl-3,4-dihydro-2H-pyrido[1,2-a]pyrimidine |
| 107 | 421.88 | 422.2/424.1/425.1 | 9-chloro-4-phenylsulfanyl-2-pyridin-2-yl-7-trifluoromethyl-3,4-dihydro-2H-pyrido[1,2-a]pyrimidine |
| 108 | 378.45 | 379.2 | 8-methyl-9-nitro-4-phenylsulfanyl-2-pyridin-2-yl-3,4-dihydro-2H-pyrido[1,2-a]pyrimidine |
| 109 | 364.42 | 365.2 | 7-nitro-4-phenylsulfanyl-2-pyridin-2-yl-3,4-dihydro-2H-pyrido[1,2-a]pyrimidine |
| 110 | 398.33 | 398.1/400.1/401.1 | 7-bromo-4-phenylsulfanyl-2-pyridin-2-yl-3,4-dihydro-2H-pyrido[1,2-a]pyrimidine |
| 111 | 364.42 | 365.2 | 9-nitro-4-phenylsulfanyl-2-pyridin-2-yl-3,4-dihydro-2H-pyrido[1,2-a]pyrimidine |
| 112 | 412.36 | 414.1/415.1 | 7-bromo-9-methyl-4-phenylsulfanyl-2-pyridin-2-yl-3,4-dihydro-2H-pyrido[1,2-a[pyrimidine |
| 113 | 412.36 | 414.1 | 4-phenylsulfanyl-2-pyridin-2-yl-3,4-dihydro-2H-pyrido]1,2-a]-9-pyrimidinol |
| 114 | 335.43 | 353.2/356.1 (M + H$_2$O) | 7-chloro-4-phenylsulfanyl-2-pyridin-2-yl-3,4-dihydro-2H-pyrido[1,2-a]pyrimidine |
| 115 | 335.43 | 336.2 | 4-phenylsulfanyl-6-propyl-2-pyridin-2-yl-3,4-dihydro-2H-pyrido[1,2-a]pyrimidine |
| 116 | 491.25 | 492.1 | 7,9-dibromo-6-methyl-4-phenylsulfanyl-2-pyridin-2-yl-3,4-dihydro-2H-pyrido[1,2-a]pyrimidine |
| 117 | 387.43 | 388.2 | 4-phenylsulfanyl-2-pyridin-2-yl-7-trifluoromethyl-3,4-dihydro-2H-pyrido[1,2-a]pyrimidine |
| 118 | 477.23 | 476.1/478.0/480.0 | 7,9-dibromo-4-phenylsulfanyl-2-pyridin-2-yl-3,4-dihydro-2H-pyrido[1,2-a]pyrimidine |
| 119 | 385.49 | 386.2 | 1-phenylsulfanyl-3-pyridin-2-yl-2,3-dihydro-1H-pyrimidine[1,2-a]-10-quinolinol |
| 120 | 289.39 | 288.4 | 2-methyl-6-pyridin-2-yl-7,10-methano-6a,7,10,10a-tetrahydro-6H-pyridol[1,2-a]quinazoline |
| 121 | 344.26 | 344.3/361.2/363.2 (M + H$_2$O) | 2,4-dichloro-6-pyridin-2-yl-7,10-methano-6a,7,10,10a-tetrahydro-6H-pyrido[1,2-a]quinazoline |
| 122 | 377.81 | 378.3/395.2/397.1 (M + H$_2$O) | 4-chloro-6-pyridin-2-yl-2-trifluoromethyl-7,10-methano-6a,7,10,10a-tetrahydro-6H-pyrido[1,2-a]quinazoline |
| 123 | 320.35 | 338.2 (M + H$_2$O) | 2-nitro-6-pyridin-2-yl-7,10-methano-6a,7,10,10a-tetrahydro-6H-pyrido[1,2-a]quinazoline |

TABLE 1-continued

| Example | Calculated mass | Actual mass | Compound |
| --- | --- | --- | --- |
| 124 | 320.35 | 338.2 (M + H$_2$O) | 4-nitro-6-pyridin-2-yl-7,10-methano-6a,7,10,10a-tetrahydro-6H-pyrido[1,2-a]quinazoline |
| 125 | 309.81 | 307.4/327.2 (M + H$_2$O) | 2-chloro-6-pyridin-2-yl-7,10-methano-6a,7,10,10a-tetrahydro-6H-pyrido[1,2-a]quinazoline |
| 126 | 317.45 | 335.3 (M + H$_2$O) | 1-propyl-6-pyridin-2-yl-7,10-methano-6a,7,10,10a-tetrahydro-6H-pyrido[1,2-a]quinazoline |
| 127 | 447.18 | 446.2/448.2/450.1 | 2,4-dibromo-1-methyl-6-pyridin-2-yl-7,10-methano-6a,7,10,10a-tetrahydro-6H-pyrido[1,2-a]quinazoline |
| 128 | 343.36 | 361.2 (M + H$_2$O) | 6-pyridin-2-yl-2-trifluoromethyl-7,10-methano-6a,7,10,10a-tetrahydro-6H-pyrido[1,2-a]quinazoline |
| 129 | 341.43 | 324.1 | 1,4-methano-5-pyridin-2-yl-1,4a,5,12c-tetrahydro-4H-6,12b-diaza-benzo[c]-12-phenathrenol |
| 130 | 325.42 | 324.2 | 1,4-methano-5-pyridin-2-yl-1,4a,5,12c-tetrahydro-4H-6,12b-diaza-benzo[c]phenathrene |
| 131 | 325.42 | 324.2 | 6-pyridin-2-yl-7,10-methano-6a,7,10,10a-tetrahydro-6H-isoquino[2,1-a]quinazoline |

Pharmaceutical Formulation of a Pharmaceutical Preparation According to the Invention 1 g of the hydrochloride of 4-(3,4-dimethoxyphenyl)-7-nitro-3,4-dihydro-2H-pyrido[1,2-a]pyrimidine 2-carboxylic acid was dissolved in 1 l of water for injection at room temperature and then adjusted to isotonic conditions by addition of sodium chloride.

What is claimed is:

1. A compound of formula I in which $R^1$ and $R^2$ independently of each other is H; OR$^{10}$; SH; SR$^{10}$; $C_{1-12}$ alkyl, which is linear or branched, saturated or unsaturated, and unsubstituted or mono- or polysubstituted; $C^{3-8}$ cycloalkyl, which is saturated or unsaturated, and unsubstituted or mono- or polysubstituted; aryl, which is unsubstituted or mono- or polysubstituted; heteroaryl, which is unsubstituted or mono- or polysubstituted; ($C_{1-6}$ alkyl)aryl, wherein the $C_{1-6}$ alkyl is linear or branched, saturated or unsaturated, and is unsubstituted or mono- or polysubstituted, and the aryl is unsubstituted or mono- or polysubstituted; or ($C_{1-6}$ alkyl)heteroaryl, wherein the $C_{1-6}$ alkyl is linear or branched, saturated or unsaturated, and unsubstituted or mono- or polysubstituted, and the heteroaryl is unsubstituted or mono- or polysubstituted, wherein one of $R^1$ and $R^2$ is H and the other of $R^1$ and $R^2$ is not H, provided that, if one of $R^1$ and $R^2$ is aryl, then the other of $R^1$ and $R^2$ is H or $C_{1-12}$ alkyl, $R^3$ and $R^4$ independently of each other is H; $C_{1-12}$ alkyl, which is linear or branched, saturated or unsaturated, and unsubstituted or mono- or polysubstituted; $C_{3-8}$ cycloalkyl, wherein the cycloalkyl is saturated or unsaturated, and unsubstituted or mono- or polysubstituted; aryl, which is unsubstituted or mono- or polysubstituted; heteroaryl, which is unsubstituted or mono- or polysubstituted; ($C_{1-6}$ alkyl)aryl, wherein the $C_{1-6}$ alkyl is linear or branched, saturated or unsaturated, and unsubstituted or mono- or polysubstituted, and the aryl is unsubstituted or mono- or polysubstituted; or ($C_{1-6}$ alkyl)heteroaryl, wherein the $C_{1-6}$ alkyl is linear or branched, saturated or unsaturated, and unsubstituted or mono- or polysubstituted, and the heteroaryl is unsubstituted or mono- or polysubstituted, wherein at least one of $R^3$ and $R^4$ is H, or one of $R^1$ or $R^2$, together with one of $R^3$ or $R^4$, forms W, wherein W means α'-(CH$_2$)$_n$-β' where n=3, 4, 5, 6, 7, 8, 9 or 10; α'-CH=CH—CH$_2$-β'; α'CH=CH—CH$_2$—CH$_2$-β'; α'-CH$_2$—CH=CH—CH$_2$-β'; α'-CH$_2$—CH$_2$—CH=CH—CH$_2$—CH$_2$-β'; α'-O—(CH$_2$)$_n$-β' where n=2, 3, 4, 5 or 6;

where X=CH$_2$, O or S, and the end of W marked & is attached to the a carbon atom of the compound of the general formula I and the end of W marked α is attached to the α carbon atom of the compound of formula I, the other of $R^1$ and $R^2$ is H or $C_{1-12}$ alkyl, wherein the alkyl is linear or branched, saturated or unsaturated, and unsubstituted or mono- or polysubstituted, and the other of $R^3$ and $R^4$ is H or $C_{1-12}$ alkyl, wherein the alkyl is linear or branched, saturated or unsaturated, and unsubstituted or mono- or polysubstituted, $R^5$ is $C_{1-12}$ alkyl, which is linear or branched, saturated or unsaturated, and unsubstituted or mono- or polysubstituted; $C_{3-8}$ cycloalkyl, which is saturated or unsaturated, and unsubstituted or mono- or polysubstituted; aryl, which is unsubstituted or mono- or polysubstituted;

heteroaryl, which is unsubstituted or mono- or polysubstituted; ($C_{1-6}$ alkyl)aryl, wherein the $C_{1-6}$ alkyl is linear or branched, saturated or unsaturated, and unsubstituted or mono- or polysubstituted, and the aryl is unsubstituted or mono- or polysubstituted; ($C_{1-6}$ alkyl) heteroaryl, wherein the $C_{1-6}$ alkyl is linear or branched, saturated or unsaturated, and unsubstituted or mono- or polysubstituted, and the heteroaryl is unsubstituted or mono- or polysubstituted; C(=O)$R^{11}$; $CO_2H$; or $CO_2R^{12}$, $R^6$, $R^7$, $R^8$ and $R^9$ independently of each other is H, F, Cl, Br, I, CN, $NH_2$, NH($C_{1-6}$ alkyl), N($C_{1-6}$ alikyl)$_2$, NH(($C_{1-6}$ alkyl)aryl), N(($C_{1-6}$ alkyl)aryl)$_2$, $NHR^{13}$, $NO_2$, OH, SH, O—$C_{1-8}$ alkyl or S(O)$_p$—$C_{1-8}$ alkyl, wherein the alkyl is linear or branched, saturated or unsaturated, and unsubstituted or mono- or polysubstituted, and p is 0, 1 or 2; O-aryl or S(O)$_q$-aryl, which is unsubstituted or mono- or polysubstituted, and q is 0, 1 or 2; O—($C_{1-6}$ alkyl)aryl or S(O)$_r$—($C_{1-6}$ alkyl)aryl, wherein the $C_{1-6}$ alkyl is linear or branched, saturated or unsaturated, and unsubstituted or mono- or polysubstituted, the aryl is unsubstituted or mono- or polysubstituted, and r is 0, 1 or 2; $CO_2H$; C(=O)$R^{14}$; $C_{1-12}$ alkyl, which is linear or branched, saturated or unsaturated, and unsubstituted or mono- or polysubstituted; $CF_3$; $C_{3-8}$ cycloalkyl, which is saturated or unsaturated, unsubstituted or mono- or polysubstituted; heterocyclyl, which is 3-, 4-, 5-, 6- or 7-membered, saturated or unsaturated, and unsubstituted or mono- or polysubstituted; aryl, which is unsubstituted or mono- or polysubstituted; or heteroaryl, which is unsubstituted or mono- or polysubstituted; or $R^6$ and $R^7$ together form Q, wherein Q means $\gamma'$-$CR^{15}$=$CR^{16}$—$CR^{17}$=$CR^{18}$-$\delta'$, the end of Q marked $\gamma'$ is attached to the $\gamma$ carbon atom of the compound of formula I and the end of Q marked $\delta'$ is attached to the $\delta$ carbon atom of the compound of formula I, and $R^8$ and $R^9$ are defined as above, or $R^6$ and $R^9$ together form T, wherein T means $\gamma'$-$CR^{19}$=$CR^{20}$—$CR^{21}$=$CR^{22}$-$\epsilon'$ or $\gamma'$-N=$CR^{20}$—$CR^{21}$=N-$\epsilon'$, the end of T marked $\gamma'$ is attached to the $\gamma$ carbon atom of the compound of formula I and the end of T marked $\epsilon$ is attached to the $\epsilon$ carbon atom of the compound of formula I, and $R^7$ and $R^8$ are defined as above, or $R^8$ and $R^9$ together form U, wherein U means $\eta'$-$CR^{19}$=$CR^{20}$—$CR^{21}$=$CR^{22}$—$\epsilon'$, the end of U marked $\eta$ is attached to the $\eta$ carbon atom of the compound of formula I and the end of U marked $\epsilon'$ is attached to the $\epsilon$ carbon atom of the compound of formula I, and $R^6$ and $R^7$ are defined as above, $R^{10}$ is $C_{1-8}$ alkyl, which is linear or branched, saturated or unsaturated, and unsubstituted or mono- or polysubstituted; $C_{3-8}$ cycloalkyl, which is saturated or unsaturated, unsubstituted or mono- or polysubstituted; aryl, which is unsubstituted or mono- or polysubstituted; heteroaryl, which is unsubstituted or mono- or polysubstituted; ($C_{1-6}$ alkyl)aryl, wherein the $C_{1-6}$ alkyl is linear or branched, saturated or unsaturated, and unsubstituted or mono- or polysubstituted, and the aryl is unsubstituted or mono- or polysubstituted; or ($C_{1-6}$ alkyl)heteroaryl, wherein the $C_{1-6}$ alkyl is linear or branched, saturated or unsaturated, and unsubstituted or mono- or polysubstituted, and the heteroaryl is unsubstituted or mono- or polysubstituted, $R^{11}$ means $NH_2$, NH($C_{1-6}$ alkyl), N($C_{1-6}$ alkyl)$_2$, NH(($C_{1-6}$ alkyl)aryl), N(($C_{1-6}$ alkyl)aryl)$^2$, $C_{1-8}$ alkyl, wherein the alkyl is linear or branched, saturated or unsaturated, and unsubstituted or mono- or polysubstituted; $C_{3-8}$ cycloalkyl, which is saturated or unsaturated, unsubstituted or mono- or polysubstituted; aryl, which is unsubstituted or mono- or polysubstituted; heteroaryl, which is unsubstituted or mono- or polysubstituted, ($C_{1-6}$ alkyl)aryl, wherein the $C_{1-6}$ alkyl is linear or branched, saturated or unsaturated, and unsubstituted or mono- or polysubstituted, and the aryl is unsubstituted or mono- or polysubstituted; or ($C_{1-6}$ alkyl)heteroaryl, wherein the $C_{1-6}$ alkyl is linear or branched, saturated or unsaturated, and unsubstituted or mono- or polysubstituted, and the heteroaryl is unsubstituted or mono- or polysubstituted;

$R^{12}$ means $C_{1-8}$ alkyl, which is linear or branched, saturated or unsaturated, and unsubstituted or mono- or polysubstituted; $C_{3-8}$ cycloalkyl, which is saturated or unsaturated, unsubstituted or mono- or polysubstituted; ($C_{1-6}$ alkyl)aryl, wherein the $C_{1-6}$ alkyl is linear or branched, saturated or unsaturated, and unsubstituted or mono- or polysubstituted, and the aryl is unsubstituted or mono- or polysubstituted, $R^{13}$ means C(=O)$CH_3$, C(=O)phenyl, C(=O)O-t.-butyl (t-BOC), $R^{14}$ means H, $NH_2$, NH($C_{1-6}$ alkyl), N($C_{1-6}$ alkyl)$_2$, NH(($C_{1-6}$ alkyl)aryl), N(($C_{1-6}$ alkyl)aryl)$_2$, $C_{1-8}$ alkyl, wherein the alkyl is linear or branched, saturated or unsaturated, and unsubstituted or mono- or polysubstituted; $C_{3-8}$ cycloalkyl, which is saturated or unsaturated, unsubstituted or mono- or polysubstituted; aryl, which is unsubstituted or mono- or polysubstituted; or ($C_{1-6}$ alkyl)aryl, wherein the $C_{1-6}$ alkyl is linear or branched, saturated or unsaturated, and unsubstituted or mono- or polysubstituted, and the aryl is unsubstituted or mono- or polysubstituted; $OC_{1-8}$ alkyl, which is linear or branched, saturated or unsaturated, and unsubstituted or mono- or polysubstituted; $OC_{3-8}$ cycloalkyl, which is saturated or unsaturated, unsubstituted or mono- or polysubstituted; aryl, which is unsubstituted or mono- or polysubstituted; or O—($C_{1-6}$ alkyl)aryl, wherein the $C_{1-6}$ alkyl is linear or branched, saturated or unsaturated, and unsubstituted or mono- or polysubstituted, and the aryl is unsubstituted or mono- or polysubstituted, $R^{15}$, $R^{16}$, $R^{17}$ and $R^{18}$ mutually independently mean H, F, Cl, Br, I, OH, CN; $C_{1-8}$ alkyl, which is linear or branched, saturated or unsaturated, and unsubstituted or mono- or polysubstituted; $CO_2H$, and $R^{19}$, $R^{20}$, $R^{21}$ and $R^{22}$ mutually independently mean H, F, Cl, Br, I, CN, OH, $C_{1-8}$ alkyl, which is linear or branched, saturated or unsaturated, and unsubstituted or mono- or polysubstituted; or $CO_2H$, or a pharmaceutically acceptable salt thereof, provided that the following compounds are excluded:
  6-chloro-2-(4-nitrophenyl)-4-phenyl-3,4-dihydro-2H-pyrido[1,2-a]pyrimidine,
  2-(4-nitrophenyl)-4-phenyl-3,4-dihydro-2H-pyrido[1,2-a]pyrimidine,
  2-(2-nitrophenyl)-4-phenyl-3,4-dihydro-2H-pyrido[1,2-a]pyrimidine,
  2-(4-nitrophenyl)-4-(4-tolyl)-3,4-dihydro-2H-pyrido[1,2-a]pyrimidine,
  2-(4-chlorophenyl)-4-(4-tolyl) -3,4-dihydro-2H-pyrido[1,2-a]pyrimidine,
  4-ethoxy-2-phenyl-3,4-dihydro-2H-pyrido[1,2-a]pyrimidine,
  4-ethoxy-2-(2-hydroxyphenyl)-3,4-dihydro-2H-pyrido[1,2-a]pyrimidine, 4-ethoxy-2-propyl-3,4-dihydro-2H-pyrido[1,2-a]pyrimidine, 4-propyl-2,3,3a,4,5,10a-hexahydro-2H-pyrido[1,2-a]furo[3,2-e]pyrimidine, and 4-propyl-2,4,4a,5,6,11a-hexahydro-2H-pyrido[1,2-a]pyrano[3,2-e]pyrimidine.

2. A compound according to claim 1, in the form of a racemate or a mixture of diastereomers or a mixture of enantiomers in any mixing ratio.

3. A compound according to claim 1, in the form of a pure enantiomer or a pure diastereomer.

4. A compounds according to claim 1, wherein
one of $R^1$ and $R^2$ is $OR^{10}$, $SR^{10}$, $C_{1-6}$ alkyl or aryl, one of $R^3$ and $R^4$ is H or $C_{1-6}$ alkyl,
or one of $R^1$ and $R^2$ together with one of $R^3$ and $R^4$ form W,
wherein W means

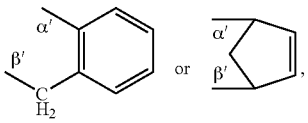

and the other two residues of $R^1$, $R^2$, $R^3$ and $R^4$ mean H or $C_{1-6}$ alkyl,
$R^5$ is $C_{3-6}$ cycloalkyl, heteroaryl, $C(=O)R^{11}$, $CO_2H$ or $CO_2R^{12}$,
$R^6$ is H, F, Cl, Br, CN, $NO_2$, $C(=O)R^{14}$, $C_{1-6}$ alkyl, $CF_3$ or aryl,
$R^7$ is H, F, Cl, Br, CN, $NH_2$, OH or $C_{1-6}$ alkyl,
or $R^6$ and $R^7$ together form Q, wherein Q means $\gamma'$-$CR^{15}$=$CR^{16}$—$CR^{17}$=$CR^{18}$-$\delta'$,
$R^8$ means H, F, Cl, Br, CN, $NO_2$, O—($C_{1-6}$ alkyl)aryl, $CO_2H$, $CONH_2$ or $C_{1-6}$ alkyl,
$R^9$ means H, OH, $CF_3$ or $C_{1-6}$ alkyl, or $R^8$ and $R^9$ together form U, wherein U means $\epsilon'$-CH=CH—CH=CH-$\eta'$,
$R^{10}$ means $C_{1-8}$ alkyl or aryl,
$R^{11}$ means aryl,
$R^{12}$ means $C_{1-6}$ alkyl,
$R^{14}$ means $OC_{1-6}$ alkyl, and
one of $R^{15}$, $R^{16}$, $R^{17}$ and $R^{18}$ means H or OH and the other residues of $R^{15}$, $R^{16}$, $R^{17}$ and $R^{18}$ mean H.

5. A compound according to claim 4, wherein
one of $R^1$ and $R^2$ is O—$(CH_2)_2$—OH, S-phenyl, $CH_3$, phenyl, 3-methyiphenyl, 2,4-dimethyiphenyl, 4-fluorophenyl, 4-hydroxyphenyl, 4-methoxyphenyl, 4-hydroxy-3-methoxyphenyl or 2-naphthyl, one of $R^3$ and $R^4$ is H or methyl, or one of $R^1$ and $R^2$ together with one of $R^3$ and $R^4$ form W,
wherein W means

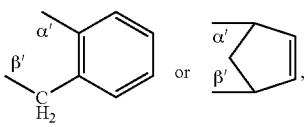

and the other two of $R^1$, $R^2$, $R^3$ and $R^4$ are H,
$R^5$ is cyclopropyl, 2-(C(=O)O-ethyl)-cyclopropyl, cyclohexyl, 2-pyridinyl, 5-methyl-2-furanyl, 5-nitro-2-furanyl, C(=O)phenyl, $CO_2H$ or $CO_2$ ethyl,
$R^6$ is H, Cl, Br, CN, $NO_2$, $CO_2$ethyl, methyl, $CF_3$ or phenyl,
$R^7$ is H, Cl, CN, $NH_2$, OH, methyl or n-propyl, or $R^6$ and $R^7$ together form Q, wherein Q is $\gamma'$-CH=CH—CH=$CR^{18}$-$\delta'$,
$R^8$ is H, Cl, Br, $NO_2$, OH, O—$CH_2$phenyl, $CO_2H$ or methyl,
$R^9$ is H or methyl,
or $R^8$ and $R^9$ together form U, wherein U means $\epsilon'$-CH=CH—CH=CH—$\eta'$,
and $R^{18}$ means H or OH.

6. A compound according to claim 1, selected from the group consisting of:

9-chloro-4-(4-methoxyphenyl)-3-methyl-7-trifluoromethyl-3,4-dihydro-2H-pyrido[1,2-a]pyrimidine 2-carboxylic acid, 9-chloro-4-(4-methoxyphenyl)-3-methyl-7-trifluoromethyl-3,4-dihydro-2H-pyrido[1,2-a]pyrimidine 2-carboxylic acid ethyl ester, 7,9-dichloro-4-(3,4-dimethoxyphenyl)-3,4-dihydro-2H-pyrido[1,2-a]pyrimidine 2-carboxylic acid ethyl ester, 7,9-dibromo-4-(3,4-dimethoxyphenyl)-3,4-dihydro-2H-pyrido[1,2-a]pyrimidine 2-carboxylic acid ethyl ester, 4-(3,4-dimethoxyphenyl)-7-nitro-3,4-dihydro-2H-pyrido[1,2-a]pyrimidine 2-carboxylic acid ethyl ester, 7,9-dichloro-4-(4-methoxyphenyl)-3,4-dihydro-2H-pyrido[1,2-a]pyrimidime 2-carboxylic acid ethyl ester, 4-(4-methoxyphenyl)-7-nitro-3,4-dihydro-2H-pyrido[1,2-a]pyrimidine 2-carboxylic acid ethyl ester, 7,9-dichloro-4-(3,4-dimethoxyphenyl)-3,4-dihydro-2H-pyrido[1,2-a]pyrimidine 2-carboxylic acid, 7,9-dibromo-4-(3,4-dimethoxyphenyl)-6-methyl-3,4-dihydro-2H-pyrido[1,2-a]pyrimidine 2-carboxylic acid, 4-(3,4-dimethoxyphenyl)-7-nitro-3,4-dihydro-2H-pyrido[1,2-a]pyrimidime 2-carboxylic acid, 7,9-dichloro-4-(4-methoxyphenyl)-3,4-dihydro-2H-pyrido[1,2-a]pyrimidime 2-carboxylic acid, 4-(4-methoxyphenyl)-7-nitro-3,4-dihydro-2H-pyrido[1,2-a]pyrimidime 2-carboxylic acid, 7-bromo-4-(4-methoxyphenyl)-9-nitro-3,4-dihydro-2H-pyrido[1,2-a]pyrimidine 2-carboxylic acid, 7,9-dichloro-4-(3,4-dimethoxyphenyl)-2-(5-nitro-2-furanyl)-3,4-dihydro-2H-pyrido[1,2-a]pyrimidine, 7,9-dibromo-4-(3,4-dimethoxyphenyl)-2-(5-nitro-2-furanyl)-3,4-dihydro-2H-pyrido[1,2-a]pyrimidime, 4-(3,4-dimethoxyphenyl)-7-nitro-2-(5-nitro-2-furanyl)-3,4-dihydro-2H-pyrido[1,2-a]pyrimidine, 7,9-dichloro-4-(4-methoxyphenyl)-2-(5-nitro-2-furanyl)-3,4-dihydro-2H-pyrido[1,2-a]pyrimidime, 2-[7,9-dichloro-4-(2,4-dimethyiphenyl)-3,4-dihydro-2H-pyrido[1,2-a]pyrimidine-2-yl]-cyclopropane carboxylic acid ethyl ester, 2-[9-chloro-4-(2,4-dimethylphenyl)-7-trifluoromethyl-3,4-dihydro-2H-pyrido[1,2-a]pyrimidine-2-yl]-cycloprop ane carboxylic acid ethyl ester, 2-[7,9-dibromo-4-(3,4-dimethoxyphenyl)-3,4-dihydro-2H-pyrido[1,2-a]-2-pyrimidinyl]-cycloprop ane carboxylic acid ethyl ester, 2-[7,9-dichloro-4-(4-methoxyphenyl)-3,4-dihydro-2H-pyrido[1,2-a]-2-pyrimidinyl]-cyclopropane carboxylic acid ethyl ester, 2-[7,9-dibromo-4-(4-methoxyphenyl)-3,4-dihydro-2H-pyrido[1,2-a]-2-pyrimidinyl]-cyclopropane carboxylic acid ethyl ester, 2-[9-chloro-4-(4-methoxyphenyl)-7-trifluoromethyl-3,4-dihydro-2H-pyrido[1,2-a]-2-pyrimidinyl]-cycloprop ane carboxylic acid ethyl ester, 2-[4-(4-methoxyphenyl)-7-nitro-3,4-dihydro-2H-pyrido[1,2-a]-2-pyrimidinyl]-cyclopropane carboxylic acid ethyl ester, 4-(4-hydroxyphenyl)-3-methyl-7-nitro-3,4-dihydro-2H-pyrido[1,2-a]pyrimidine 2-carboxylic acid ethyl ester, 7,9-dichloro-4-phenylsulfanyl-3,4-dihydro-2H-pyrido[1,2-a]pyrimidine 2-carboxylic acid, 7-nitro-4-phenylsulfanyl-3,4-dihydro-2H-pyrido[1,2-a]pyrimidine 2-carboxylic acid, 7,9-dichloro-4-(4-hydroxy-3-methoxyphenyl)-3-methyl-3,4-dihydro-2H-pyrido[1,2-a]pyrimidine 2-carboxylic acid, 7,9-dibromo-4-(4-hydroxy-3-methoxyphenyl)-3-methyl-3,4-dihydro-2H-pyrido[1,2-a]pyrimidine 2-carboxylic acid, 7,9-dibromo-4-(4-hydroxy-3-methoxyphenyl)-3,6-dimethyl-3,4-dihydro-2H-pyrido[1,2-a]pyrimidine 2-carboxylic acid, 9-chloro-4-(4-hydroxy-3-methoxyphenyl)-3-methyl-7-trifluoromethyl-3,4-dihydro-2H-pyrido[1,2-a]pyrimidine 2-carboxylic acid, 7,9-dichloro-4-(4-methoxyphenyl)-3-methyl-3,4-dihydro-2H-pyrido[1,2-a]pyrimidine 2-carboxylic acid, 7,9-dibromo-4-(4-methoxyphenyl)-3-methyl-3,4-dihydro-2H-pyrido[1,2-a]pyrimidime 2-carboxylic acid ethyl ester, 7,9-dibromo-4-(4-methoxyphenyl)-3-methyl-3,4-dihydro-2H-pyrido[1,2-a]pyrimidine 2-carboxylic acid, 7,9-dibromo-4-(4-methoxyphenyl)-3,6-dimethyl-3,4-dihydro-2H-pyrido[1,2-a]pyrimidine 2-carboxylic acid, 9-chloro-4-(4-methoxyphenyl)-3-methyl-7-trifluoromethyl-3,4-dihydro-2H-pyrido[1,2-a]pyrimidine 2-carboxylic acid, 4-(4-methoxyphenyl)-3-methyl-7-nitro-3,4-dihydro-2H-pyrido[1,2-a]pyrimidine 2-carboxylic acid, 7-bromo-4-(4-methoxyphenyl)-3-methyl-9-nitro-3,4-dihydro-2H-pyrido[1,2-a]pyrimidine 2-carboxylic acid, 7,9-dichloro-4-(4-hydroxyphenyl)-3-methyl-3,4-dihydro-2H-pyrido[1,2-a]pyrimidine 2-carboxylic acid, 7,9-dibromo-4-(4-hydroxyphenyl)-3,6-dimethyl-3,4-dihydro-2H-pyrido[1,2-a]pyrimidime 2-carboxylic acid, 7,9-dichloro-4-(3,4-dimethoxyphenyl)-3,4-dihydro-2H-pyrido[1,2-a]pyrimidine 2-carboxylic acid, 7,9-dibromo-4-(3,4-dimethoxyphenyl)-3,4-dihydro-2H-pyrido[1,2-a]pyrimidine 2-carboxylic acid, 7,9-dibromo-4-(3,4-dimethoxyphenyl)-6-methyl-3,4-dihydro-2H-pyrido[1,2-a]pyrimidine 2-carboxylic acid, 9-chioro-4-(3,4-dimethoxyphenyl)-7-trifluoromethyl-3,4-dihydro-2H-pyrido[1,2-a]pyrimidine 2-carboxylic acid, 4-(3,4-dimethoxyphenyl)-7-nitro-3,4-dihydro-2H-pyrido[1,2-a]pyrimidine 2-carboxylic acid, 7,9-dichloro-4-(4-methoxyphenyl)-3,4-dihydro-2H-pyrido[1,2-a]pyrimidine 2-carboxylic acid, 7,9-dibromo-4-(4-methoxyphenyl)-3,4-dihydro-2H-pyrido[1,2-a]pyrimidine 2-carboxylic acid, 7,9-dibromo-4-(4-methoxyphenyl)-6-methyl-3,4-dihydro-2H-pyrido[1,2-a]pyrimidine 2-carboxylic acid, 9-chioro-4-(4-methoxyphenyl)-7-trifluoromethyl-3,4-dihydro-2H-pyrido[1,2-a]pyrimidine 2-carboxylic acid, 4-(4-methoxyphenyl)-7-nitro-3,4-dihydro-2H-pyrido[1,2-a]pyrimidine 2-carboxylic acid,

[7,9-dichloro-4-(4-hydroxy-3-methoxyphenyl)-3-methyl-3,4-dihydro-2H-pyrido[1,2-a]-2-pyrimidinyl]-phenylmethanone,

[7,9-dibromo-4-(4-hydroxy-3-methoxyphenyl)-3-methyl-3,4-dihydro-2H-pyrido[1,2-a]-2-pyrimidinyl]-phenylmethanone,

[7,9-dibromo-4-(4-hydroxy-3-methoxyphenyl)-3,6-dimethyl-3,4-dihydro-2H-pyrido[1 2-a]-2-pyrimidinyl]-phenylmethanone

[4-(4-hydroxy-3-methoxyphenyl)-3-methyl-7-nitro-3,4-dihydro-2H-pyrido[1,2-a]-2-pyrimidinyl]-phenylmethanone,

[4-(4-methoxyphenyl)-3-methyl-7-nitro-3,4-dihydro-2H-pyrido[1,2-a]-2-pyrimidinyl]-phenylmethanone,

[7,9-dibromo-4-(4-hydroxyphenyl)-3,6-dimethyl-3,4-dihydro-2H-pyrido[1,2-a]-2-pyrimidinyl]-phenylmethanone,

[7,9-dichloro-4-(3,4-dimethoxyphenyl)-3,4-dihydro-2H-pyrido[1,2-a]-2-pyrimidinyl]-phenylmethanone,

[7,9-dibromo-4-(3,4-dimethoxyphenyl)-3,4-dihydro-2H-pyrido[1,2-a]-2-pyrimidinyl]-phenylmethanone,

[7,9-dibromo-4-(3,4-dimethoxyphenyl)-6-methyl-3,4-dihydro-2H-pyrido[1,2-a]-2-pyrimidinyl]-phenylmethanone,

[9-chloro-4-(3,4-dimethoxyphenyl)-7-trifluoromethyl-3,4-dihydro-2H-pyrido[1,2-a]-2-pyrimidinyl]-phenylmethanone,

[4-(3,4-dimethoxyphenyl)-7-nitro-3,4-dihydro-2H-pyrido[1,2-a]-2-pyrimidinyl]-phenylmethanone,

[4-(4-methoxyphenyl)-7-nitro-3,4-dihydro-2H-pyrido[1,2-a]-2-pyrimidinyl]-phenylmethanone, 2-(7,9-dichloro-2-cyclopropyl-3,4-dihydro-2H-pyrido[1,2-a]-4-pyrimidinyloxy)-ethanol, 2-(7,9-dibromo-2-cyclopropyl-3,4-dihydro-2H-pyrido[1,2-a]-4-pyrimidinyloxy)-ethanol, 2-(9-chioro-2-cyclopropyl-7-trifluoromethyl-3,4-dihydro-2H-pyrido[1,2-a]-4-pyrimidinyloxy)-ethanol, 2-(2-cyclopropyl-7-nitro-3,4-dihydro-2H-pyrido[1,2-a]-4-pyrimidinyloxy)-ethanol, 9-chloro-2-cyclopropyl-4-(3,4-dimethoxyphenyl)-7-trifluoro methyl-3,4-dihydro-2H-pyrido[1,2-a]pyrimidine, 7,9-dibromo-2-cyclopropyl-4-(4-methoxyphenyl)-3,4-dihydro-2H-pyrido[1,2-a]pyrimidine, 9-chloro-2-cyclopropyl-4-(4-methoxyphenyl)-7-trifluoromethyl-3,4-dihydro-2H-pyrido[1,2-a]pyrimidine, 2-cyclopropyl-4-(4-methoxyphenyl)-7-nitro-3,4-dihydro-2H-pyrido[1,2-a]pyrimidine, 2-(7,9-dichloro-2-cyclohexyl-3,4-dihydro-2H-pyrido[1,2-a]-4-pyrimidinyloxy)-ethanol, 2-(7,9-dibromo-2-cyclohexyl-3,4-dihydro-2H-pyrido[1,2-a]-4-pyrimidinyloxy)-ethanol, 2-(7,9-dibromo-2-cyclohexyl-6-methyl-3,4-dihydro-2H-pyrido[1,2-a]-4-pyrimidinyloxy)-ethanol, 2-(9-chloro-2-cyclohexyl-7-trifluoromethyl-3,4-dihydro-2H-pyrido[1,2-a]-4-pyrimidinyloxy)-ethanol, 2-(2-cyclohexyl-7-nitro-3,4-dihydro-2H-pyrido[1,2-a]-4-pyrimidinyloxy)-ethanol, 7,9-dichloro-2-cyclohexyl-4-(3,4-dimethoxyphenyl)-3,4-dihydro-2H-pyrido[1,2-a]pyrimidine, 7,9-dichloro-2-cyclohexyl-4-(4-methoxyphenyl)-3,4-dihydro-2H-pyrido[1,2-a]pyrimidine, 7,9-dibromo-2-cyclohexyl-4-(4-methoxyphenyl)-3,4-dihydro-2H-pyrido[1,2-a]pyrimidine, 9-chioro-2-cyclohexyl-4-(4-methoxyphenyl)-7-trifluoromethyl-3,4-dihydro-2H-pyrido[1,2-a]pyrimidine, 7,9-dibromo-4-(4-methoxyphenyl)-3-methyl-3,4-dihydro-2H-pyrido[1,2-a]pyrimidine 2-carboxylic acid ethyl ester, 7,9-dibromo-4-(4-methoxyphenyl)-3-methyl-3,4-dihydro-2H-pyrido[1,2-a]pyrimidine 2-carboxylic acid, 7,9-dibromo-4-(4-methoxyphenyl)-3-methyl-2-(5-nitro-2-furanyl)-3,4-dihydro-2H-pyrido[1,2-a]pyrimidine, 2-[7,9-dibromo-4-(4-methoxyphenyl)-3-methyl-3,4-dihydro-2H-pyrido[1,2-a]-2-pyrimidinyl]-cyclopropane carboxylic acid ethyl ester,
7,9-dibromo-4-(3,4-dimethoxyphenyl)-6-methyl-2-(5-nitro-2-furanyl)-3,4-dihydro-2H-pyrido[1,2-a]pyrimidine,
4-(4-methoxyphenyl)-7-nitro-2-(5-nitro-2-furanyl)-3,4-dihydro-2H-pyrido[1,2-a]pyrimidine,
2-[7,9-dibromo-4-(2,4-dimethylphenyl)-3,4-dihydro-2H-pyrido[1,2-a]-2-pyrimidinyl]-cyclopropane carboxylic acid ethyl ester,
2-[7,9-dibromo-4-(3,4-dimethoxyphenyl)-6-methyl-3,4-dihydro-2H-pyrido[1,2-a]-2-pyrimidinyl]-cyclopropane carboxylic acid ethyl ester,
2-[9-chloro-4-(3,4-dimethoxyphenyl)-7-trifluoromethyl-3,4-dihydro-2H-pyrido[1,2-a]-2-pyrimidinyl]-cyclopropane carboxylic acid ethyl ester,
2-[7,9-dibromo-4-(4-methoxyphenyl)-6-methyl-3,4-dihydro-2H-pyrido[1,2-a]-2-pyrimidinyl]-cyclopropane carboxylic acid ethyl ester,
2-[4-(4-fluorophenyl)-4-methyl-7-nitro-3,4-dihydro-2H-pyrido[1,2-a]-2-pyrimidinyl]-cyclopropane carboxylic acid ethyl ester,
9-benzyloxy-4-phenyl-2-pyridin-2-yl-3,4-dihydro-2H-pyrido[1,2-a]pyrimidine,
8-methyl-7-nitro-4-phenyl-2-pyridin-2-yl-3,4-dihydro-2H-pyrido[1,2-a]pyrimidine,
7,9-dichloro-4-phenyl-2-pyridin-2-yl-3,4-dihydro-2H-pyrido[1,2-a]pyrimidine,
9-chloro-4-phenyl-2-pyridin-2-yl-7-trifluoromethyl-3,4-dihydro-2H-pyrido[1,2-a]pyrimidine,
8-methyl-9-nitro-4-phenyl-2-pyridin-2-yl-3,4-dihydro-2H-pyrido[1,2-a]pyrimidine,
7-nitro-4-phenyl-2-pyridin-2-yl-3,4-dihydro-2H-pyrido[1,2-a]pyrimidine,
9-nitro-4-phenyl-2-pyridin-2-yl-3,4-dihydro-2H-pyrido[1,2-a]pyrimidine,
7-bromo-9-nitro-4-phenyl-2-pyridin-2-yl-3,4-dihydro-2H-pyrido[1,2-a]pyrimidine,
7,9-dibromo-6-methyl-4-phenyl-2-pyridin-2-yl-3,4-dihydro-2H-pyrido[1,2-a]pyrimidine,
7,9-dibromo-4-phenyl-2-pyridin-2-yl-3,4-dihydro-2H-pyrido[1,2-a]pyrimidine,
4-phenylsulfanyl-2-pyridin-2-yl-3,4- dihydro -2H-pyrido[1,2-a]pyrimidine -9-carboxylic acid,
7-methyl-4-phenylsulfanyl-2-pyridin-2-yl-3,4-dihydro-2H-pyrido[1,2-a]pyrimidime,
9-benzyloxy-4-phenylsulfanyl-2-pyridin-2-yl-3,4-dihydro-2H-pyrido[1,2-a]pyrimidine,
8-methyl-7-nitro-4-phenylsulfanyl-2-pyridin-2-yl-3,4-dihydro-2H-pyrido[1,2-a]pyrimidine,
6-chloro-9-nitro-4-phenylsulfanyl-2-pyridin-2-yl-3,4-dihydro-2H-pyrido[1,2-a]pyrimidine,
7,9-dichloro-4-phenylsulfanyl-2-pyridin-2-yl-3,4-dihydro-2H-pyrido[1,2-a]pyrimidime,
9-chloro-4-phenylsulfanyl-2-pyridin-2-yl-7-trifluoromethyl-3,4-dihydro-2H-pyrido[1,2-a]pyrimidine,
8-methyl-9-nitro-4-phenylsulfanyl-2-pyridin-2-yl-3,4-dihydro-2H-pyrido[1,2-a]pyrimidine,
7-nitro-4-phenylsulfanyl-2-pyridin-2-yl-3,4-dihydro-2H-pyrido[1,2-a]pyrimidime,
7-bromo-4-phenylsulfanyl-2-pyridin-2-yl-3,4-dihydro-2H-pyrido[1,2-a]pyrimidime,
9-nitro-4-phenylsulfanyl-2-pyridin-2-yl-3,4-dihydro-2H-pyrido[1,2-a]pyrimidine,
7-bromo-9-methyl-4-phenylsulfanyl-2-pyridin-2-yl-3,4-dihydro-2H-pyrido[1,2-a]pyrimidine,
4-phenylsulfanyl-2-pyridin-2-yl-3,4-dihydro-2H-pyrido[1,2-a]-9-pyrimidinol,
7-chloro-4-phenylsulfanyl-2-pyridin-2-yl-3,4-dihydro-2H-pyrido[1,2-a]pyrimidime,
4-phenylsulfanyl-6-propyl-2-pyridin-2-yl-3,4-dihydro-2H-pyrido[1,2-a]pyrimidine,
7,9-dibromo-6-methyl-4-phenylsulfanyl-2-pyridin-2-yl-3,4-dihydro-2H-pyrido[1,2-a]pyrimidine,
4-phenylsulfanyl-2-pyridin-2-yl-7-trifluoromethyl-3,4-dihydro-2H-pyrido[1,2-a]pyrimidine,
7,9-dibromo-4-phenylsulfanyl-2-pyridin-2-yl-3,4-dihydro-2H-pyrido[1,2-a]pyrimidine,
1-phenylsulfanyl-3-pyridin-2-yl-2, 3-dihydro-1H-pyrimidine [1,2-a]-10-quinolinol,
2-methyl-6-pyridin-2-yl-7,10-methano-6a,7,10,10a-tetrahydro-6H-pyrido[1,2-a]quinazoline,
2,4-dichloro-6-pyridin-2-yl-7,10-methano-6a,7,10,10a-tetrahydro-6H-pyrido[1,2-a]quinazoline,
4-chloro-6-pyridin-2-yl-2-trifluoromethyl-7,10-methano-6a,7,10,10a-tetrahydro-6H-pyrido[1,2-a]quinazoline,
2-nitro-6-pyridin-2-yl-7,10-methano-6a,7,10,10a-tetrahydro-6H-pyrido[1,2-a]quinazoline,
4-nitro-6-pyridin-2-yl-7,10-methano-6a,7,10,10a-tetrahydro-6H-pyrido[1,2-a]quinazoline,
2-chloro-6-pyridin-2-yl-7,10-methano-6a,7,10,10a-tetrahydro-6H-pyrido[1,2-a]quinazoline,
1-propyl-6-pyridin-2-yl-7,10-methano-6a,7,10,10a-tetrahydro-6H-pyrido[1,2-a]quinazoline,
2,4-dibromo-1-methyl-6-pyridin-2-yl-7,10-methano-6a,7,10,10a-tetrahydro-6H-pyrido[1,2-a]quinazoline,
6-pyridin-2-yl-2-trifluoromethyl-7,10-methano-6a,7,10,10a-tetrahydro-6H-pyrido[1,2-a]quinazoline,
1,4-methano-5-pyridin-2-yl-1,4a,5,12c-tetrahydro-4H-6,12b-diaza-benzo [c]-12-phenathrenol,
1,4-methano-5-pyridin-2-yl-1,4a,5,12c-tetrahydro-4H-6,12b-diaza-benzo[c]phenathrene, and
6-pyridin-2-yl-7,10-methano-6a,7,10,10a-tetrahydro-6H-isoquino [2,1-a]quinazoline.

7. A process for producing a compound according to claim 1, the method comprising
reacting, in the presence of an acid, a compound of formula II

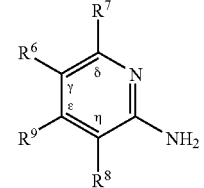

in which $R^6$ and $R^7$ are as defined for formula I, provided that,
if $R^6$ and $R^7$ form Q, the end of Q marked γ' is attached to the γ carbon atom of formula II and the end of Q marked δ' is attached to the δ carbon atom of formula II, if $R^6$ and $R^9$ form T, the end marked γ' is attached to the γ carbon atom of formula II and the end marked ε' is attached to the ε carbon atom of formula II, and if $R^8$ and $R^9$ form U, the end marked η' is attached to the η carbon atom of formula II and the end marked ε' is attached to the ε carbon atom of formula II, with a compound of formula III

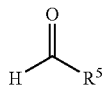

in which R⁵ is as defined for formula I, and a compound of formula IV

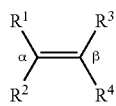

in which $R^1$, $R^2$, $R^3$ and $R^4$ are as defined for formula I, provided that, if one of $R^1$ and $R^2$, together with one of $R^3$ and $R^4$, forms W, the end of W marked α' is attached to the α carbon atom of formula IV and the end of W marked β' is attached to the β carbon atom of formula IV.

8. A process according to claim 7, wherein the reaction of the compound of formula II with the compound of formula III and the compound of formula IV is performed in a single-vessel reaction.

9. A process according to claim 7, wherein the acid is trifluoroacetic acid.

10. A process according to claim 7, wherein the reaction is performed in an organic solvent at a temperature of between about 0 to 100° C. and a reaction time of between about 0.25 to 12 h.

11. A process according to claim 9, wherein the reaction is performed at a temperature of between about 15 to 40° C.

12. A process according to claim 10, wherein the organic solvent is acetonitrile.

13. A substance library comprising at least one compound according to claim 1.

14. A pharmaceutical preparation comprising at least one compound selected from the group consisting of 6-chloro-2-(4-nitrophenyl)-4-phenyl-3,4-dihydro-2H-pyrido[1,2-a]pyrimidine, 2-(4-nitrophenyl)-4-phenyl-3,4-dihydro-2H-pyrido[1,2-a]pyrimidine, 2-(2-nitrophenyl)-4-phenyl-3,4-dihydro-2H-pyrido[1,2-a]pyrimidine, 2-(4-nitrophenyl)-4-(4-tolyl)-3,4-dihydro-2H-pyrido[1,2-a]pyrimidine, 2-(4-chlorophenyl)-4-(4-tolyl)-3,4-dihydro-2H-pyrido[1,2-a]pyrimidine, 4-ethoxy-2-phenyl-3,4-dihydro-2H-pyrido[1,2-a]pyrimidine, 4-ethoxy-2-(2-hydroxyphenyl)-3,4-dihydro-2H-pyrido[1,2-a]pyrimidine, 4-ethoxy-2-propyl-3,4-dihydro-2H-pyrido[1,2-a]pyrimidine, 4-propyl-2,3,3a,4,5,10a-hexahydro-2H-pyrido[1,2-a]furo[3,2-e]pyrimidine, 4-propyl-2,4,4a, 5,6,11a-hexahydro-2H-pyrido[1,2-a]pyrano [3,2-e]pyrimidine, and a compound according to claim 1, or a pharmaceutically acceptable salt thereof, and a pharmaceutically acceptable excipient.

* * * * *